(12) United States Patent
Roe et al.

(10) Patent No.: US 7,838,720 B2
(45) Date of Patent: Nov. 23, 2010

(54) ABSORBENT ARTICLE HAVING A WETNESS EVENT COUNTER

(75) Inventors: Donald Carroll Roe, West Chester, OH (US); Robin Lynn McKiernan, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 712 days.

(21) Appl. No.: 11/400,633

(22) Filed: Apr. 7, 2006

(65) Prior Publication Data

US 2006/0229578 A1   Oct. 12, 2006

Related U.S. Application Data

(63) Continuation-in-part of application No. 11/100,653, filed on Apr. 7, 2005.

(51) Int. Cl.
*A61F 13/15* (2006.01)
*A61F 13/20* (2006.01)

(52) U.S. Cl. ............................... 604/361; 604/362

(58) Field of Classification Search ............. 604/361, 604/362
See application file for complete search history.

(56) References Cited

U.S. PATENT DOCUMENTS

| | | | |
|---|---|---|---|
| 3,759,246 A | 9/1973 | Flack et al. | |
| 3,848,594 A | 11/1974 | Buell | |
| 3,860,003 A | 1/1975 | Buell | |
| 4,022,211 A | 5/1977 | Timmons et al. | |
| 4,163,449 A | 8/1979 | Regal | |
| 4,231,370 A | 11/1980 | Mroz et al. | |
| 4,381,781 A | 5/1983 | Sciaraffa et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,681,576 A | 7/1987 | Colon et al. | |
| 4,699,622 A | 10/1987 | Toussant et al. | |
| 4,705,513 A * | 11/1987 | Sheldon et al. | 604/361 |
| 4,743,238 A | 5/1988 | Colon et al. | |
| 4,834,733 A * | 5/1989 | Huntoon et al. | 604/361 |
| 4,834,735 A | 5/1989 | Alemany et al. | |
| 4,846,815 A | 7/1989 | Scripps | |
| 4,857,067 A | 8/1989 | Wood et al. | |

(Continued)

FOREIGN PATENT DOCUMENTS

CN   1211416 A   3/1999

(Continued)

OTHER PUBLICATIONS

Translation of JP2004-208833.*

(Continued)

*Primary Examiner*—Tatyana Zalukaeva
*Assistant Examiner*—Ginger T Chapman
(74) *Attorney, Agent, or Firm*—Laura L. Whitmer; John G. Powell; Amy M. Foust

(57) ABSTRACT

A wetness event counter, which can be utilized in a disposable absorbent article, has at least one indicating member. The indicating member can provide a first indication to a caregiver for a first wetness event and a second indication, which is different from the first indication, to a caregiver upon a second wetness event.

12 Claims, 13 Drawing Sheets

U.S. PATENT DOCUMENTS

| | | | |
|---|---|---|---|
| 4,888,231 A | 12/1989 | Angstadt | |
| 4,894,060 A | 1/1990 | Nestegard | |
| 4,895,567 A | 1/1990 | Colon et al. | |
| 4,938,753 A | 7/1990 | Van Gompel et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,990,147 A | 2/1991 | Freeland | |
| 5,035,691 A | 7/1991 | Zimmel et al. | |
| 5,062,840 A | 11/1991 | Holt et al. | |
| 5,066,711 A | 11/1991 | Colon et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,755 A | 12/1993 | Bodicky | |
| 5,306,266 A | 4/1994 | Freeland | |
| 5,342,338 A | 8/1994 | Roe | |
| 5,342,861 A | 8/1994 | Raykovitz | |
| 5,354,289 A * | 10/1994 | Mitchell et al. | 604/361 |
| 5,387,207 A | 2/1995 | Dyer et al. | |
| 5,397,318 A | 3/1995 | Dreier | |
| 5,435,010 A | 7/1995 | May | |
| 5,499,978 A | 3/1996 | Buell et al. | |
| 5,507,736 A | 4/1996 | Clear et al. | |
| 5,514,121 A | 5/1996 | Roe et al. | |
| 5,537,095 A | 7/1996 | Dick et al. | |
| 5,540,671 A | 7/1996 | Dreier | |
| 5,554,142 A | 9/1996 | Dreier et al. | |
| 5,554,145 A | 9/1996 | Roe et al. | |
| 5,569,234 A | 10/1996 | Buell et al. | |
| 5,570,082 A | 10/1996 | Mahgerefteh et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,625,222 A | 4/1997 | Yoneda et al. | |
| 5,650,222 A | 7/1997 | DesMarais et al. | |
| 5,653,703 A | 8/1997 | Roe et al. | |
| 5,669,897 A | 9/1997 | Lavon et al. | |
| 5,760,694 A | 6/1998 | Nissim et al. | |
| 5,766,212 A * | 6/1998 | Jitoe et al. | 604/361 |
| 5,790,035 A | 8/1998 | Ho | |
| 5,851,611 A * | 12/1998 | Guttag | 428/35.7 |
| 5,865,823 A | 2/1999 | Curro | |
| 5,897,545 A | 4/1999 | Kline et al. | |
| 5,938,648 A | 8/1999 | LaVon et al. | |
| 5,941,864 A | 8/1999 | Roe | |
| 5,957,908 A | 9/1999 | Kline et al. | |
| 5,977,430 A | 11/1999 | Roe et al. | |
| 5,997,520 A | 12/1999 | Ahr et al. | |
| 6,004,306 A | 12/1999 | Robles et al. | |
| 6,010,490 A | 1/2000 | Freeland et al. | |
| 6,013,063 A | 1/2000 | Roe et al. | |
| 6,013,589 A | 1/2000 | DesMarais et al. | |
| 6,075,178 A | 6/2000 | La Wilhelm et al. | |
| 6,083,211 A | 7/2000 | DesMarais | |
| 6,120,487 A | 9/2000 | Ashton | |
| 6,120,489 A | 9/2000 | Johnson et al. | |
| 6,168,584 B1 | 1/2001 | Allen et al. | |
| 6,187,696 B1 | 2/2001 | Lim et al. | |
| 6,203,496 B1 * | 3/2001 | Gael et al. | 600/362 |
| 6,284,942 B1 * | 9/2001 | Rabin | 604/361 |
| 6,297,424 B1 | 10/2001 | Olson et al. | |
| 6,307,119 B1 | 10/2001 | Cammarota et al. | |
| 6,432,097 B1 * | 8/2002 | Ahr et al. | 604/385.19 |
| 6,432,098 B1 | 8/2002 | Kline et al. | |
| 6,627,786 B2 | 9/2003 | Roe et al. | |
| 6,635,797 B2 | 10/2003 | Olson et al. | |
| 6,710,221 B1 * | 3/2004 | Pierce et al. | 604/361 |
| 6,772,708 B2 * | 8/2004 | Klofta et al. | 116/206 |
| 2001/0031954 A1 | 10/2001 | Jordan et al. | |
| 2001/0053898 A1 * | 12/2001 | Olson et al. | 604/361 |
| 2002/0007162 A1 | 1/2002 | Cammarota et al. | |
| 2003/0100872 A1 | 5/2003 | Roe et al. | |
| 2003/0137425 A1 | 7/2003 | Gabriel | |
| 2003/0233082 A1 | 12/2003 | Kline et al. | |
| 2005/0027267 A1 | 2/2005 | Van Dyke et al. | |
| 2005/0070867 A1 | 3/2005 | Beruda et al. | |
| 2006/0069360 A1 * | 3/2006 | Long et al. | 604/361 |
| 2008/0145945 A1 | 6/2008 | Song | |
| 2008/0147030 A1 | 6/2008 | Nhan et al. | |
| 2008/0147031 A1 | 6/2008 | Long et al. | |

FOREIGN PATENT DOCUMENTS

| | | |
|---|---|---|
| DE | 36 08 114 A1 | 9/1987 |
| DE | 29715536 U1 | 11/1997 |
| EP | 0 847 738 A1 | 6/1998 |
| JP | 03-264060 A | 11/1991 |
| JP | 10-151154 A | 6/1998 |
| JP | 2004-208833 * | 7/2004 |
| JP | 2004-222868 | 8/2004 |
| WO | WO 95/00099 A1 | 1/1995 |
| WO | WO 02/36177 * | 5/2002 |
| WO | WO 02/36177 A2 | 5/2002 |

OTHER PUBLICATIONS

PCT International Search Report.

* cited by examiner

ABSORBENT ARTICLE HAVING A WETNESS EVENT COUNTER

CROSS REFERENCE TO RELATED APPLICATION

This application is a continuation-in-part of application Ser. No. 11/100,653 filed on Apr. 7, 2005.

FIELD OF THE INVENTION

The invention relates to hygienic absorbent articles, such as diapers, adult incontinence articles, and the like including a wetness event counter. More particularly, the invention is directed to an absorbent article having a wetness event counter which indicates the number of times the absorbent article has been wetted.

BACKGROUND OF THE INVENTION

Absorbent articles are widely used by infants and incontinent individuals to receive and contain body exudates. There are currently many absorbent articles available which provide a wetness indication feature. In general, the wetness indicator becomes visible or disappears upon urination by a wearer. Also available, are absorbent articles which provide a visible indication of the remaining capacity of the absorbent article. However, these wetness indications can do little in the way of providing information regarding the number of times the wearer has urinated.

The wetness indication can do little in the way of providing the caregiver or a physician with information concerning the urination tendencies of the wearer. The number of urination events can provide useful information to the caregiver or physician concerning potential urinary problems with the wearer, if an unusually high number of wetness events occur in a short period of time or if an unusually low number of wetness events occur over a long period of time.

Moreover, counting or keeping track of the number of urination events experienced by the wearer could be useful as a continence training tool. In general, two important issues with regard to continence training are the bladder capacity of the wearer, and the ability to control the urethral sphincter muscle. Typically, higher bladder capacity and greater ability to control the urethral sphincter muscle equate to more successful continence training. For example, younger children, i.e. infants, because of their smaller bladder capacity, may have to urinate more frequently than an older child would. Smaller bladder capacity may inhibit continence training. In addition, these younger children may lack the ability to control the urethral sphincter muscle which could also inhibit continence training.

The number of urination events can provide the caregiver with information about the readiness of the child as well as whether or not the child has developed control over the urethral sphincter. For, example, the caregiver may note that the wearer urinates only once in a four hour period whereas previously the wearer urinated at least twice. This information could be indicative of an increase in bladder size or control over the urethral sphincter.

Also, the number of urination events can provide the caregiver with feedback regarding the successfulness of the continence training. For example, the caregiver may note that after continence training, the wearer urinates less frequently than previously, e.g. once in a four hour period versus twice in a four hour period which is indicative of some success in continence training.

Consequently, there is a need for an absorbent article with the capability to detect the number of wetness events experienced by the absorbent article. In addition, there is a need for an absorbent article which can provide the caregiver with a signal indicating the number of wetness events experienced by the absorbent article.

SUMMARY OF THE INVENTION

The present invention pertains to an absorbent article having a wetness event counter adapted for wearing about the lower torso of a wearer. The absorbent article comprises a chassis which includes a topsheet, a backsheet which is attached to at least a portion of the topsheet, and an absorbent core disposed between the topsheet and the backsheet.

The wetness event counter is attached to the chassis and comprises an indicating member. The indicating member provides a visible signal when dry and can provide an obstructed signal when activated.

In one embodiment, the absorbent article is a disposable pull-on diaper having a wearer-facing surface and a garment-facing surface; a longitudinal axis and a lateral axis; and a front waist region, a back waist region, and a crotch region disposed between the front and back waist regions. The front waist region and back waist region are joined to form a waist opening and leg openings.

The disposable pull-on diaper further comprises a topsheet and a backsheet which is attached to at least a portion of the topsheet. The backsheet has an inner surface and an outer surface. An absorbent core is disposed between at least a portion of the topsheet and the backsheet.

A wetness event counter is attached to the inner surface of the backsheet, wherein the wetness event counter comprises a first indicating member, a second indicating member, a third indicating member, and a fourth indicating member. The first indicating member provides a visible signal when dry and is adaptable to provide an obstructed signal when activated by a first wetness event. The second indicating member provides a visible signal when dry and is adaptable to provide an obstructed second signal when activated by a second wetness event.

DETAILED DESCRIPTION OF THE INVENTION

Definitions

Figure 1:
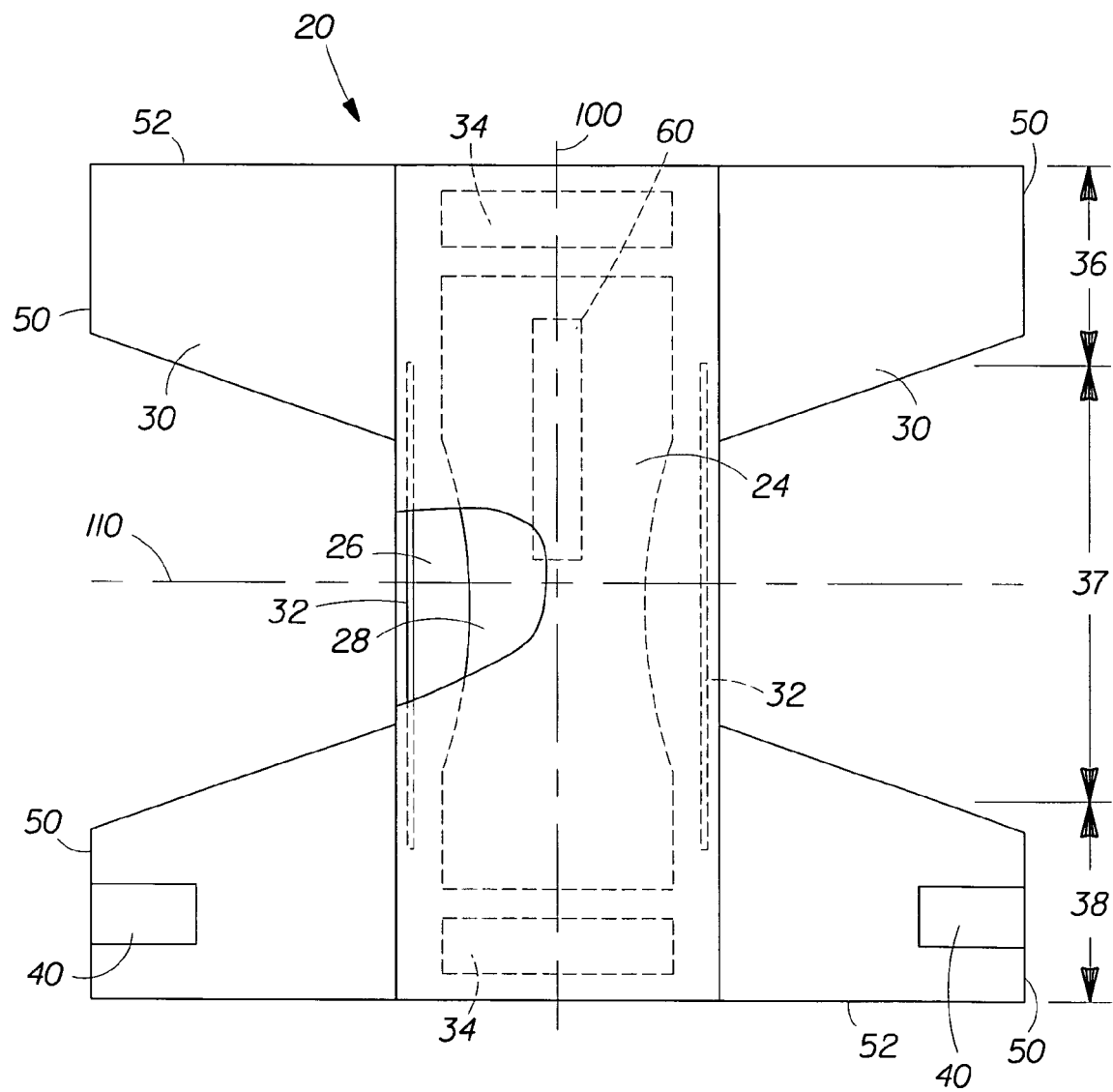
FIG. 1 shows a cut away view of a disposable absorbent article in a flattened, uncontracted, condition, the disposable absorbent article comprising a wetness event counter in accordance with the present invention.

As used herein, the following terms have the following meanings:

As used herein, the term "absorbent article" refers to devices that absorb and contain body exudates and, more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner). The present invention is also applicable to other wearable and absorbent articles such as incontinence briefs, incontinence undergarments, absorbent inserts, diaper holders and liners, feminine hygiene garments, bandages and the like.

As used herein, the term "activate" shall mean to produce an intended action or effect. Any terms conjugated from the term "activate", shall retain the above meaning in the correct conjugated form. In addition, the term "activation" shall refer to the act of producing an intended action or effect.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein the term "different" when used in the context of the visible signals means any change in color, contrast, tint, shape, size, distance, location, the like, or a combination thereof, of the previous indication to the latter indication.

As used herein, the term "disposed" refers to an element being attached and positioned in a particular place or position in a unitary structure with other elements.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction and in the same plane as the longitudinal direction. Directions within ±45° of the lateral direction are considered to be "lateral".

The term "orthogonal" refers to a direction that is generally at a right angle to the plane in which the "longitudinal" direction and the "lateral" direction lie. Directions within ±80° of the orthogonal direction are considered to be "orthogonal".

As used herein the term "moisture" includes but is not limited to water, urine, or feces. The moisture can be in a liquid or vapor state.

The terms "pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

The term "obstruct" means to impede or retard the view of an otherwise visible signal.

The terms "permeable" and "impermeable" refer to the penetrability of materials in the context of the intended usage of disposable absorbent articles. Specifically, the term "permeable" refers to a layer or a layered structure having pores or openings that permit liquid water to pass through its thickness in the absence of a forcing pressure. Conversely, the term "impermeable" refers to a layer or a layered structure through the thickness of which liquid water cannot pass in the absence of a forcing pressure. As is well known in the art, a common method for measuring the permeability of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

DESCRIPTION

The present invention is a disposable absorbent article comprising a wetness event counter. The wetness event counter can be utilized in a number of different absorbent articles. For example, in a disposable diaper, the wetness event counter can provide a caregiver with useful information concerning the urinary or defecation tendencies of a wearer by counting the number of wetness events. As another example, in a catamenial product, the wetness event counter can count the number of menses events. Despite the fact that the wetness event counter of the present invention can be incorporated into many different absorbent articles, for the sake of explanation, the present invention will be discussed in the context of a diaper. However, similar embodiments are available in the absorbent articles mentioned heretofore.

FIG. 1 is a plan view of the diaper 20 of the present invention in a flat-out, uncontracted, state with portions of the structure being cut-away to more clearly show the construction of the diaper 20. The portion of the diaper 20 that faces a wearer is oriented towards the viewer. As shown in FIG. 1, the diaper 20 comprises a topsheet 24; a backsheet 26; and an absorbent core 28 that is positioned between at least a portion of the topsheet 24 and the backsheet 26. The absorbent article further comprises side panels 30, elasticized leg cuffs 32, elastic waist features 34, and a fastening system generally designated 40. The diaper 20 has a first waist region 36, a second waist region 38 opposed to the first waist region 36, and a crotch region 37 located between the first waist region 36 and the second waist region 38. The periphery of the diaper 20 is defined by the outer edges of the diaper 20 in which longitudinal edges 50 run generally parallel to a longitudinal centerline 100 of the diaper 20 and end edges 52 run between the longitudinal edges 50 generally parallel to a lateral centerline 110 of the diaper 20.

The diaper 20 further comprises a wetness event counter 60 which can produce a signal indicating the number of wetness events experienced by the diaper 20. For example, the signal can be a visible indication of the number of times the wearer has urinated. In another example, the signal can be a visible indication of the number of times the wearer has defecated in conjunction with or independently from the number of times the wearer has urinated. Alternative to or in conjunction with the visible indication, the signal can be an audible, tactile, or olfactory, indication, or any combination thereof. For the sake of explanation, visible indications shall be discussed with regard to the embodiments mentioned herein.

The wetness event counter 60 may be located at any point in the absorbent article likely to be contacted by exudates from the wearer. For example, in one embodiment, the wetness event counter 60 can be located in the portion of the article in communication with the urine loading point (i.e., the location in which the urine typically insults the article, such as in the vicinity of the longitudinal centerline 100 of the article in the crotch region 37 of the article). In another embodiment, the wetness event counter 60 may be located remotely from the urine loading point and may comprise an intermediate wicking member which transports moisture from the urine loading point to the wetness event counter 60.

In addition, the wetness event counter 60 may be attached to any component of the article but should be in communication with the urine loading point. For example, the wetness event counter 60 may be attached to the topsheet 24, the absorbent core 28, or the backsheet 26. In one embodiment, wetness event counter 60 is positioned between the topsheet 24 and the absorbent core 28 and provides a signal that is visible through the topsheet, such as when a waist edge is pulled away from the body of the wearer to enable inspection of the interior of the article. In another embodiment, the wetness event counter 60 may be positioned between the backsheet 26 and the absorbent core 28, such that the signal provided by the wetness event counter can be seen through at least a portion of the backsheet. In yet another embodiment, the wetness event counter 60 may be disposed on the article in such a way that a patch or portion of the article can be pulled away, permanently or temporarily, to expose the counter such that the signal is visible without the article being removed from the wearer. In yet another embodiment, a separate element which is applied to the absorbent article by the caregiver, such as a diaper insert or other carrier element affixed to an element of the diaper 20 (e.g., via adhesive, a mechanical fastener, friction, etc.) by the caregiver prior to applying the diaper to the wearer may comprise the wetness event counter 60.

Figure 2A:
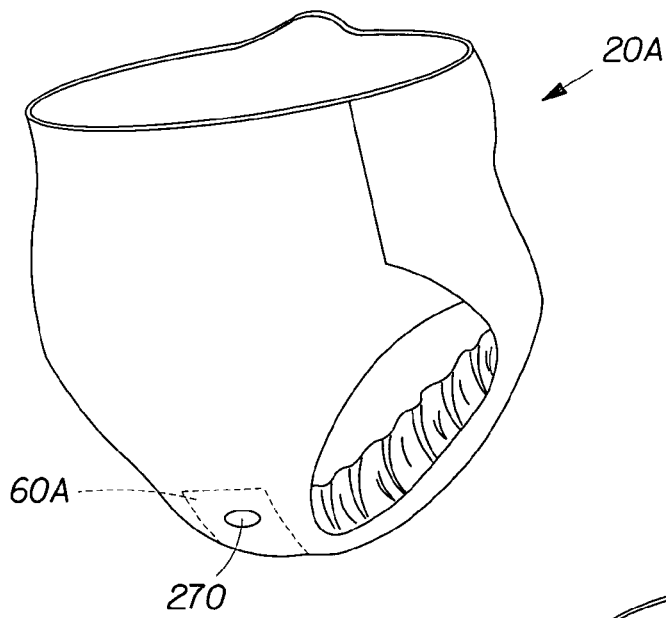
FIGS. 2A-2C show different embodiments of the wetness event counter of FIG. 1 in a pant type absorbent article.
Figure 2B:
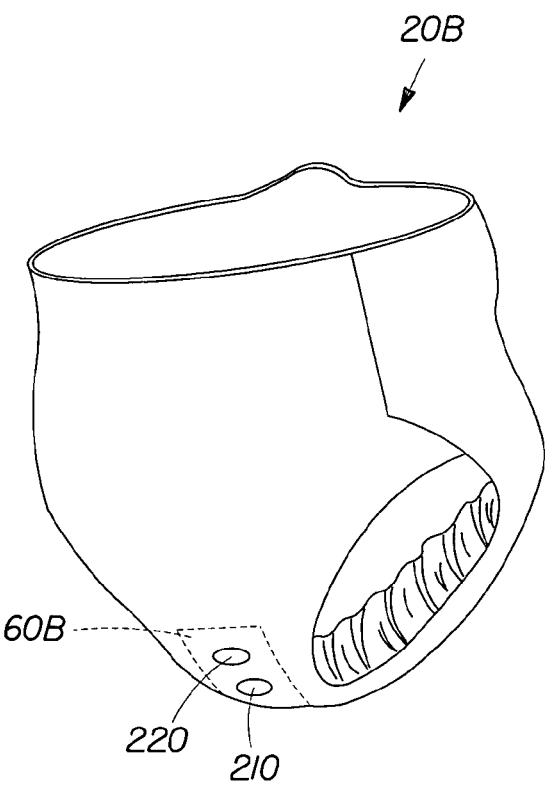
Figure 2C:
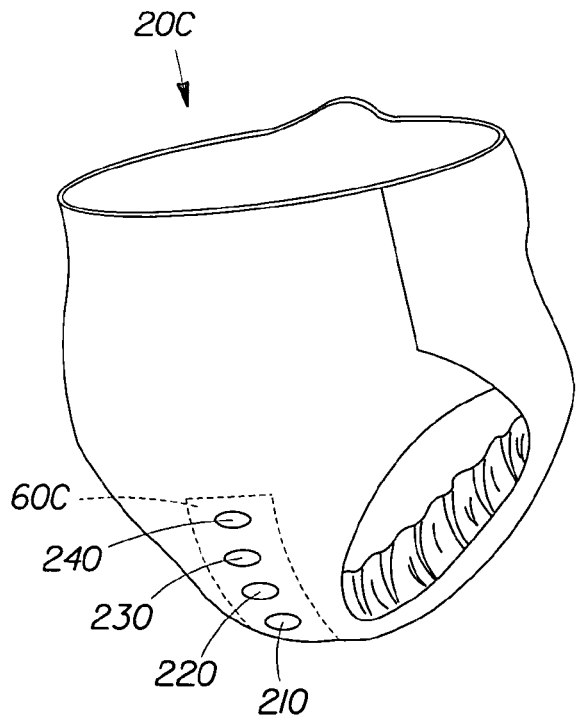

As shown in FIGS. 2A-2C, in some embodiments, a wetness event counter may be incorporated into pant type absorbent articles. In addition, the wetness event counter may comprise a single indicating member or a plurality of indicating members. As shown in FIG. 2A, a pant 20A comprises a wetness event counter 60A which may comprise a single indicating member 270. The single indicating member 270 can provide a first signal for a first wetness event and a second signal, which is different from the first signal, for a second wetness event. For example, a first wetness event, may cause a first signal which is a visible indication that is blue, while a second wetness event, may cause a second signal which is a separate visible indication which is yellow. Therefore the caregiver could see a blue indication and a yellow indication which correlates to the first and second wetness events, respectively. In yet another example, the second signal can modify the first signal, e.g. yellow combines with blue to form green, to provide a single visible indication of the second wetness event.

As shown in FIG. 2B, a pant 20B comprises a wetness event counter 60B which may comprise a first indicating member 210 and a second indicating member 220. A first wetness event activates the first indicating member 210 thereby causing the first indicating member 210 to provide a first signal. In some embodiments, the first signal can be a visible indication, i.e. appearing upon the first wetness event. In some embodiments, the first signal can be an obstructed indication, i.e. becoming obstructed upon a first wetness event. As an example, the first signal can be a color change or appearance on the backsheet of the article. Subsequently, a second wetness event activates the second indicating member 220 thereby causing the second indicating member 220 to provide a second signal. The second signal can be configured similarly to the first signal. Namely, upon a second wetness event the second signal can appear or become obstructed. For example, the second signal may include a separate visible indication from the first visible indication, or the second visible indication may change the shape or the size of the first signal.

As shown in FIG. 2C, a pant 20C comprises a wetness event counter 60C which may comprise a third indicating member 230 and a fourth indicating member 240, in addition to the first indicating member 210 and the second indicating member 220 of FIG. 2B. The operation of the wetness event counter 60C is similar to that of the wetness event counter 60B (shown in FIG. 2B). However, the wetness event counter 60 C can provide visible indications of a third and a fourth wetness event via the third and the fourth indicating members 230 and 240.

Embodiments are contemplated where a first indication is provided for a first wetness event and a subsequent indication is provided when the number of wetness events is greater than one. Also, embodiments, are contemplated where a first indication is provided for a first wetness event, a second indication is provided for a second wetness event, and a subsequent indication is provided when the number of wetness events exceeds two.

Additionally, embodiments where graphics or visible indications are initially present and become obstructed when wetted are contemplated. For example, the disposable absorbent article, when dry, may comprise a plurality of indicating members providing a plurality of visible indications which are blue. Upon a first wetness event, a first indicating member can dissipate such that the visible indication of the first indicating member is obstructed through the backsheet. Similarly, upon a second wetness event the visible indication of a second indicating member can dissipate such that the visible indication of the second indicating member is obstructed through the backsheet.

Any suitable material can be utilized to provide visible indication when dry and obstructed indication or no indication when wet. For example, the indicating members may comprise an ink which is visible when the disposable article is in a dry state and which dissipates when wetted. Some suitable examples include an ink available under the designation CRNFS 561179 which is available from Sun Chemicals® and an ink available under the designation 5307 which is available from Videojet®.

Other embodiments including graphics or visible indications which are initially present and become obstructed when wetted are contemplated. For example, the disposable absorbent article, when dry, may comprise a plurality of indicating members which provide yellow visible indications. Upon a first wetness event, the visible indication of the first indicating member can turn blue. In some embodiments, a background may comprise a first color which matches the activated color of the indicating member, e.g. blue, such that the activated color is no distinguishable from the color of the background. For example, an indicating member can provide a yellow indication when dry and a blue indication when activated. So, as an example, a blue background can be chosen such that upon a wetness event, the blue indication would be indistinguishable from the blue background.

Any suitable material can be utilized to provide visible indications when dry and a different visible indication when wet. For example, some materials, as discussed in the example above can provide an initially yellow indication when dry; however, upon being wetted can provide a blue visible indication. Some suitable examples of materials which can provide a first visible indication when dry and a second visible indication (different from the first visible indication) when wet are sold under the designation of H9219-01, H9052, and H9133-05, available from Bostik®.

In some embodiments, the first indicating member may comprise a combination of two dyes which form a first color. For example, the dyes can be selected such that a first dye or the second dye is water soluble. Therefore, upon a wetness event, the first dye or the second dye can dissolve. In doing so, the visible indication can change from a first color to a second color. As an example, the two dyes may comprise yellow and blue such that the first color of the visible indication is green. Upon a wetness event, the blue dye can be selected such that the blue dye dissolves and the yellow dye does not dissolve. Thus, the visible indication can change from green to yellow upon a wetness event.

Figure 3A:
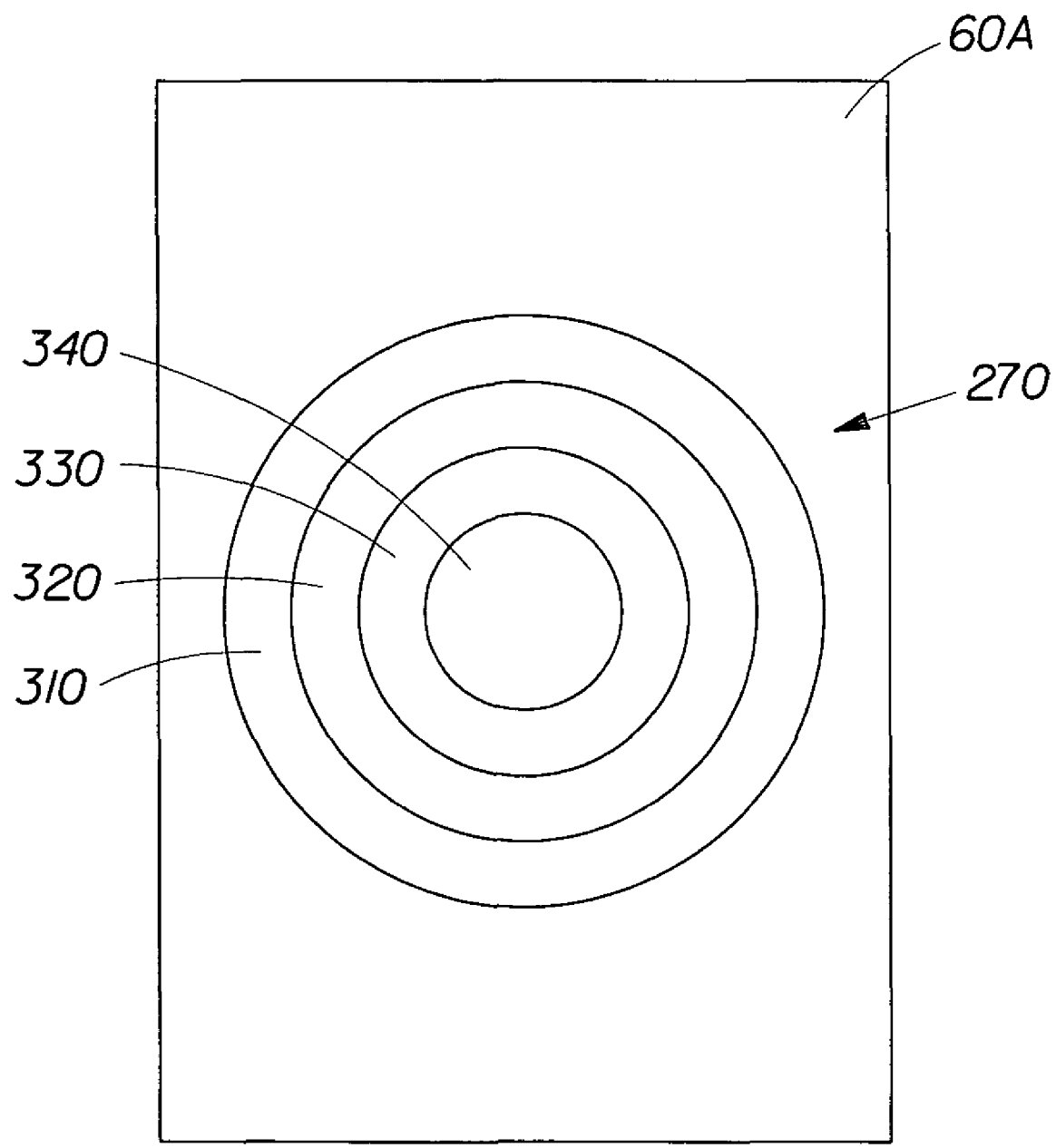
FIG. 3A shows an embodiment of an indicating member of FIG. 2A.
Figure 3B:
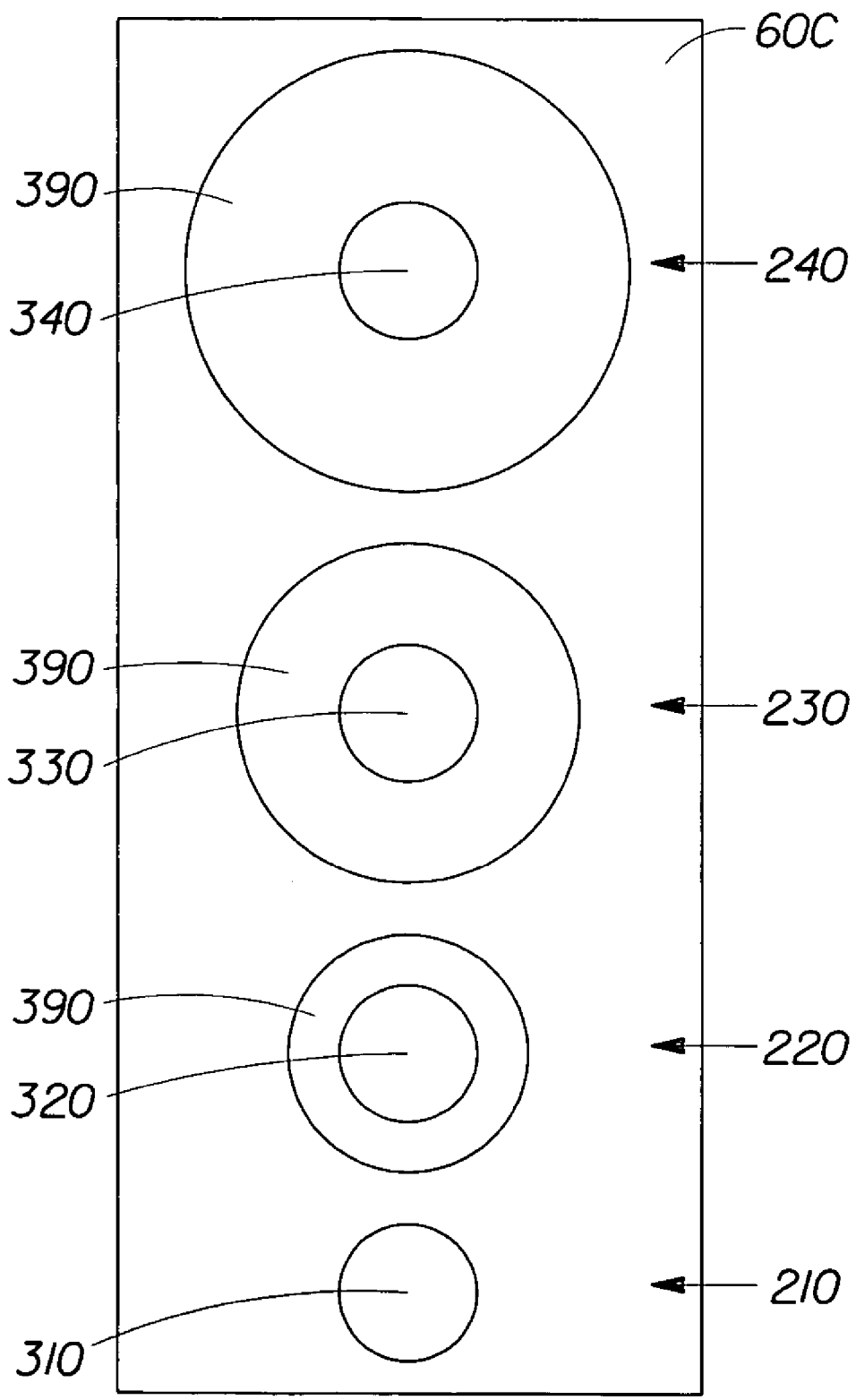
FIG. 3B shows an embodiment of a plurality of indicating members of FIG. 2C.
Figure 3C:
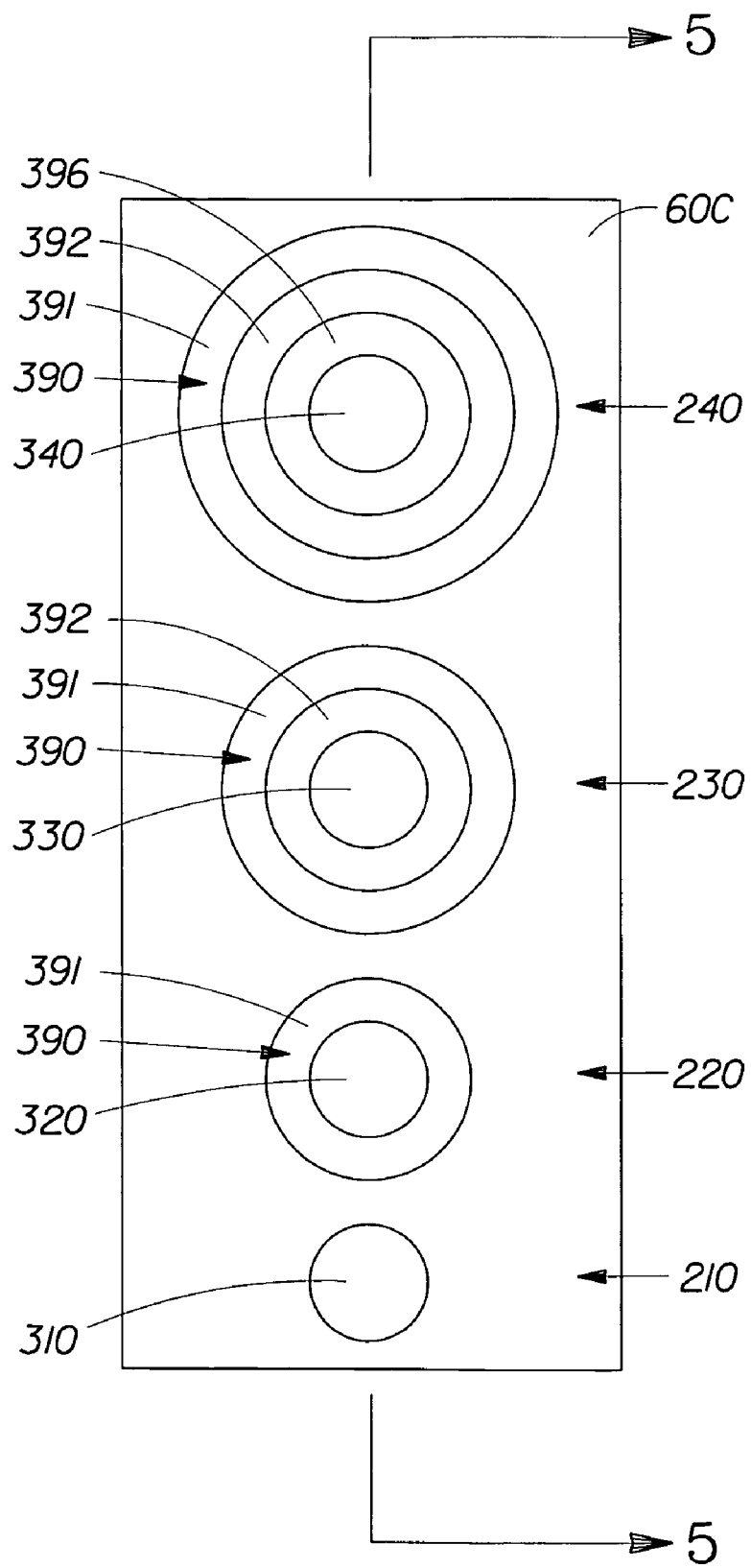
FIG. 3C shows another embodiment of the plurality of indicating member of FIG. 2C.

As shown in FIGS. 3A-3C, the indicating members may comprise multiple layers. While the multiple layers shown in these figures are substantially concentric, there is no requirement that the layers be concentric. Similarly, there is no requirement that the multiple layers are substantially disc shaped. Instead, the multiple layers may be in many different shapes. For example, as shown in FIGS. 3A and 3B, the multiple layers may be in a generally annular shape or in a generally spherical shape (if spherical, then a cross section through the center of each sphere is shown). Any shape known in the art can be used for the layers.

As shown in FIG. 3A, the wetness event counter 60A may comprise a single indicating member 270. The single indicating member 270 may comprise a first reactive element 310 and a second reactive element 320 surrounded by the first reactive element 310. The single indicating member 270 may further comprise a third reactive element 330 and a fourth reactive element 340 wherein the third reactive element 330 is surrounded by the second reactive element 320 and the fourth reactive element 340 is surrounded by the third reactive element 330.

The wetness event counter 60A should be positioned within the diaper such that moisture from the wearer can be in communication with the wetness event counter 60A and can activate the reactive elements of the single indicating member 270. Upon a first wetness event, moisture from the wearer activates the first reactive element 310 thereby causing the first reactive element 310 to provide a visible indication of the first wetness event. In addition to providing a visible indication, the first reactive element 310 may also preclude the activation of the second reactive element 320 upon the first wetness event, thereby preventing a false indication. In one embodiment, the first reactive element 310 may comprise a barrier layer which precludes activation of the second reactive element 320 upon the first wetness event. In another embodiment, the second reactive element 320 can be selected such that activation does not occur on a first wetness event.

Upon a second wetness event, moisture from the wearer activates the second reactive element 320 thereby causing the second reactive element 320 to provide a visible indication of the second wetness event. The visible indication of the second reactive element 320 should be different from the visible indication provided by the first reactive element 310 such that a caregiver can distinguish the first wetness event from the second wetness event. For example, upon the first wetness event, the first reactive element 310 could provide a visible indication which appears as a yellow dot. Subsequently, upon the second wetness event, the second reactive element 320 could provide a visible indication which independently appears as a blue ring surrounding the yellow dot. Alternatively, upon the second wetness event, the second reactive element 320 may provide a visible indication which modifies the visible indication provided by the first reactive element 310. For example, the second reactive element 320 could modify the yellow dot of the first reactive element 310 such that upon a second wetness event, a green dot appears. As another example, the second reactive element 320 can modify the yellow dot of the first reactive element 310 such that the size of the yellow dot is increased. In addition, similar to the first reactive element 310, the second reactive element 320 may also preclude the activation of the third reactive element 330, thereby preventing a false indication in a manner similar to that described above with respect to the first reactive element 310.

Upon a third wetness event, moisture from the wearer activates the third reactive element 330, thereby causing the third reactive element 330 to provide a visible indication of the third wetness event. The visible indication of the third reactive element 330 should be different from the visible indication provided by the second reactive element 320 such that a caregiver can distinguish the second wetness event from the third wetness event. The difference between the indication of the third reactive element 330 and the second reactive element 320 can be similar to that described above with regard to the difference between the visible indications of the first reactive element 310 and the second reactive element 320. In addition, similar to the first reactive element 310, the third reactive element 330 may also preclude the activation of the fourth reactive element 340, thereby preventing a false indication in a manner similar to that described above with respect to the first reactive element 310.

Upon a fourth wetness event, moisture from the wearer activates the fourth reactive element 340, thereby causing the fourth reactive element 340 to provide a visible indication of the fourth wetness event. The visible indication of the fourth reactive element 340 should be different from the visible indication provided by the third reactive element 330 such that a caregiver can distinguish the fourth wetness event from the third wetness event. The difference between the indication of the fourth reactive element 340 and the third reactive element 330 can be similar to that described above with regard to the difference between the indications of the first reactive element 310 and the second reactive element 320.

As shown in FIG. 3B, the wetness event counter 60C may comprise a plurality of indicating members. The wetness event counter 60C should be positioned within the disposable diaper such that moisture from the wearer can be in communication with the wetness event counter 60C and can activate the reactive elements of the plurality of indicating members.

Each of the indicating members in this embodiment comprises a reactive element, i.e. first reactive element 310, second reactive element 320, third reactive element 330, and a fourth reactive element 340. The second, third, and fourth indicating members 220, 230, and 240, may each further comprise a non-reactive element 390. The non-reactive elements 390 preclude the second, third, and fourth reactive elements 320, 330, and 340, from being activated prematurely. For example, moisture from a first wetness event activates the first reactive element 310, thereby causing a visible indication of the first wetness event. In contrast, the non-reactive elements 390 can preclude moisture from the first wetness event from activating the second reactive element 320, the third reactive element 330, and the fourth reactive element 340.

The non-reactive elements 390 can be selected such that subsequent wetness events are allowed to activate their respective indicating members. For example, the non-reactive element 390 of the second indicating member 220 can be selected such that moisture from a second wetness event activates the second reactive element 320. In contrast, the non-reactive elements 390 of the third and fourth indicating members 230 and 240 can be selected such that moisture from the second wetness event is absorbed and activation of their respective reactive elements is thereby precluded. The non-reactive element 390 for the third indicating member 230 can be similarly selected such that moisture from a third wetness event activates the third reactive element 330. Also, the non-reactive element 390 for the fourth indicating member 240 can be selected such that moisture from the third wetness event is precluded from activating the fourth reactive element 340.

As shown in FIG. 3C, the non-reactive elements 390 may comprise a plurality of non-reactive portions or a single non-reactive portion. For example, as shown in FIG. 3C, the non-reactive elements 390 of the second indicating member 220, the third indicating member 230, and the fourth indicating member 240, each may comprise a first non-reactive portion 391. The first non-reactive portions 391, as described above with respect to the non-reactive element 390, should preclude activation of the second reactive element 320, the third reactive element 330, and the fourth reactive element 340, upon the first wetness event. For example, the first non-reactive portions 391 may be selected such that they absorb moisture from the first wetness event, thereby precluding premature activation of the reactive elements. However, upon a second wetness event, the first non-reactive portions 391 could then allow moisture to pass through to second non-reactive portions 392 or the second reactive element 320.

The non-reactive elements 390 of the third indicating member 230 and the fourth indicating member 240 may further comprise second non-reactive portions 392. The second non-reactive portions 392 can preclude the activation of the third reactive element 330 and the fourth reactive element 340 upon the second wetness event in the same manner as described above with regard to the first non-reactive portions 391. Therefore, upon a third wetness event, the second non-reactive portion 392 could allow moisture to pass through the first non-reactive portions 391 and the second non-reactive portions 392 to the third reactive element 330 or to a third non-reactive portion 396.

The non-reactive element 390 of the fourth indicating member 240 may further comprise a third non-reactive portion 396. The third non-reactive portion 396 can preclude the activation of the fourth reactive element 340 upon the third wetness event. As discussed above with respect to the first non-reactive portions 391 and the second non-reactive portions 392, the third non-reactive portion 396 can also be selected such that it absorbs moisture from the third wetness event or multiple wetness events such that any moisture in communication with the fourth indicating member 240 prior to the fourth wetness event is absorbed in the third non-reactive portion 396 or the non-reactive portions discussed heretofore.

Note that the embodiments discussed in regard to FIGS. 3A-3C allow for the cumulative counting of wetness events. Specifically, a portion of the first indicating member 210 can provide a visible indication of a wetness event and maintain that visible indication throughout subsequent wetness events. Similarly, the second, third, and fourth indicating members 220, 230, and 240, can also maintain their visible indications for subsequent wetness events. However, the indicating members can be configured such that a visible indication from a prior wetness event is affected on a subsequent wetness event. A visible indication may be affected in many different ways. For example, a subsequent wetness event may affect the previous visible indication by causing the previous visible indication to disappear or by masking, or covering the previous visible indication or by obstructing the previous visible indication. In another example, a subsequent wetness event may affect a previous visible indication by causing a change in color, contrast, tint, shape, size, or a combination thereof, of the previous visible indication.

Figure 4A:
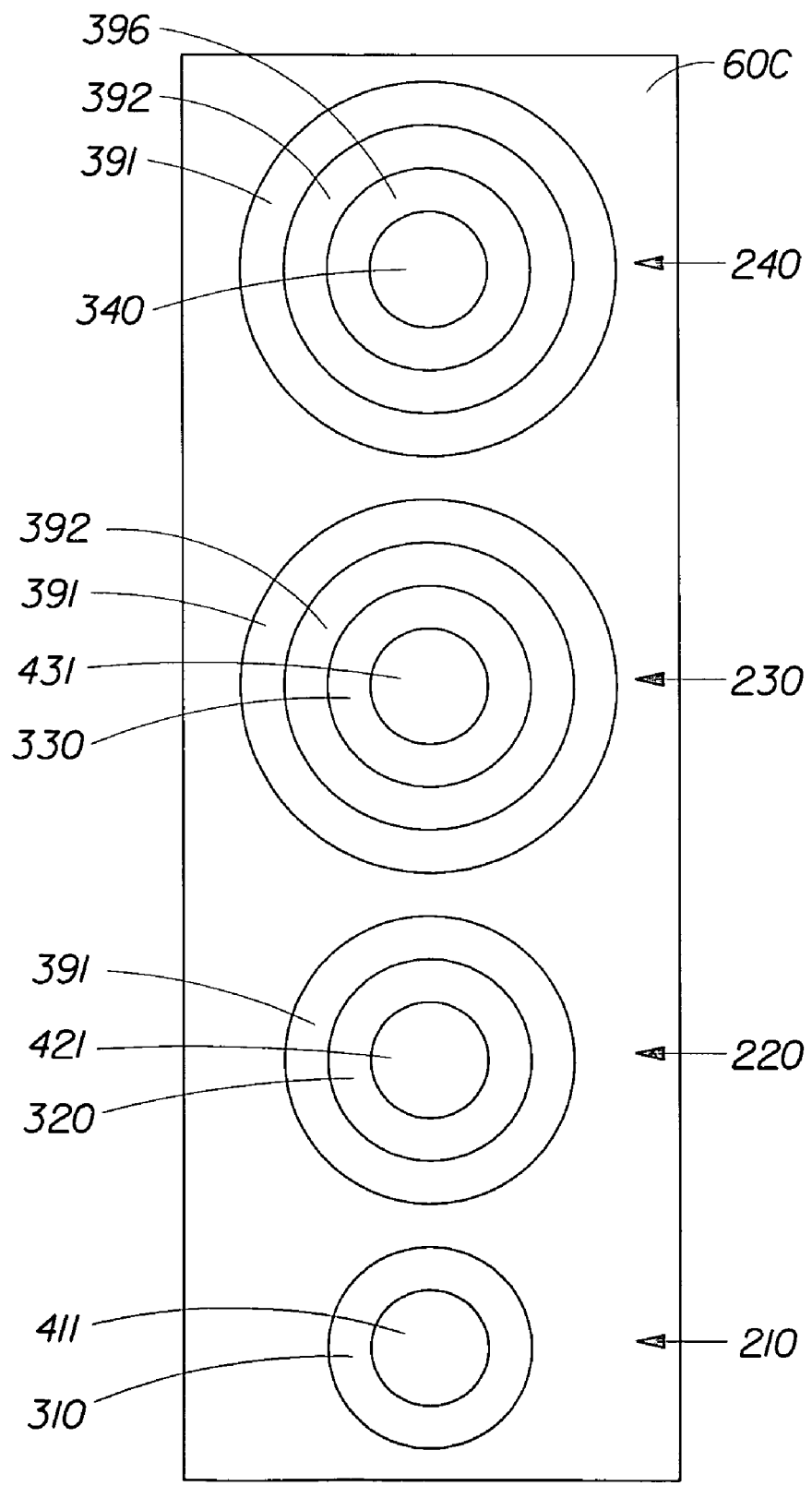
FIG. 4A shows another embodiment of the plurality of indicting members of FIG. 2C with the additional feature of counter-acting elements.

FIG. 4A shows an embodiment of the present invention wherein the visible indications of previous wetness events can be affected on subsequent wetness events. Similar to the embodiments shown in FIGS. 3B and 3C, each of the indicating members in this embodiment comprises a reactive element, i.e. first reactive element 310, second reactive element 320, third reactive element 330, and a fourth reactive element 340. However, the first, second, and third indicating members 210, 220, and 230 may each further comprise counter-acting elements. Specifically, the first indicating member 210 may further comprise a first counter-acting element 411, the second indicating member 220 may further comprise a second counter-acting element 421, and the third indicating member 230 may comprise a third counter-acting element 431.

The operation of the indicating members in this embodiment is similar to that discussed above with respect to the embodiments shown in FIGS. 3B and 3C. As discussed previously, moisture from a first wetness event can activate the first reactive element 310 such that a visible indication of the first wetness event is provided by the first reactive element 310. However, moisture from a second wetness event can activate the first counter-acting element 411 thereby causing the first counter-acting element 411 to affect the visible indication provided by the first reactive area 310. Note that the first counter-acting element 411 can be selected such that subsequent wetness events, beyond the second wetness event, have no effect on the first counter-acting element 411.

Similarly, moisture from a third wetness event can activate the second counter-acting element 421, thereby causing the second counter-acting element 421 to affect the visible indication provided by the second reactive element 320. Similar to the first counter-acting element 411, the second counter-acting element 421 can be configured such that subsequent wetness events, beyond the third wetness event, have no effect on the second counter-acting element 421.

Moisture from a fourth wetness event can activate the third counter-acting element 431, thereby causing the third counter-acting element 431 to affect the visible indication provided by the third reactive element 330. Similar to the first counter-acting element 411 and the second counter-acting element 421, the third counter-acting element 431 can be configured such that subsequent wetness events beyond the fourth wetness event have no effect on the third counter-acting element 431.

Figure 4B:
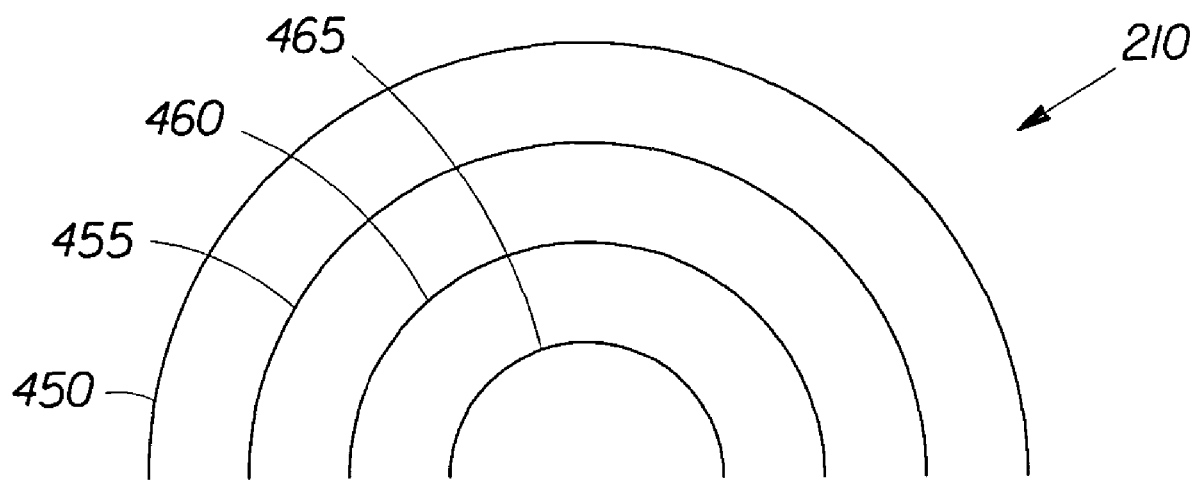
FIG. 4B shows an embodiment of an indicating member of the embodiment of FIG. 4A.

Regarding FIG. 4B, another embodiment of the present invention wherein the visible indications of previous wetness events can be affected on subsequent wetness events is shown. In this embodiment, the first indicating member 210 may comprise a first protective layer 450, a first reactive layer 455, a second protective layer 460, and a second reactive layer 465. Moisture from a first wetness event may transfer through the first protective layer 450 and activate the first reactive layer 455 such that a visible indication is provided to indicate the first wetness event. The second protective layer 460 can be positioned such that moisture from the first wetness event does not activate the second reactive layer 465. However, moisture from a second wetness event may transfer through the second protective layer 460 and activate the second reactive layer 465. The activation of the second reactive layer 465 can alter the visible indication provided by the first reactive layer 455 as described above with regard to FIG. 4A and the counter-acting elements.

Note that only the first indicating member 210 is shown; however, the subsequent indicating members may be configured in the same manner as the first indicating member 210. Additional protective layers may be added to the subsequent indicating members as required. Alternatively, an individual protective layer for a subsequent indicating member can be selected such that it precludes activation of a reactive layer from the moisture of multiple wetness events.

The indicating members of the present invention should be configured such that the correct reactive element, reactive layer, or counter-acting element is activated by moisture from a specific wetness event. For example, the reactive element of the second indicating member should be activated by moisture from a second wetness event. Thus, the second indicating member should be configured such that moisture from a first wetness event does not activate the reactive element of the second indicating member. There are many ways to configure the indicating members such that their respective reactive elements, reactive layers, or counter-acting elements are activated by moisture from the proper wetness event.

Figure 5A:
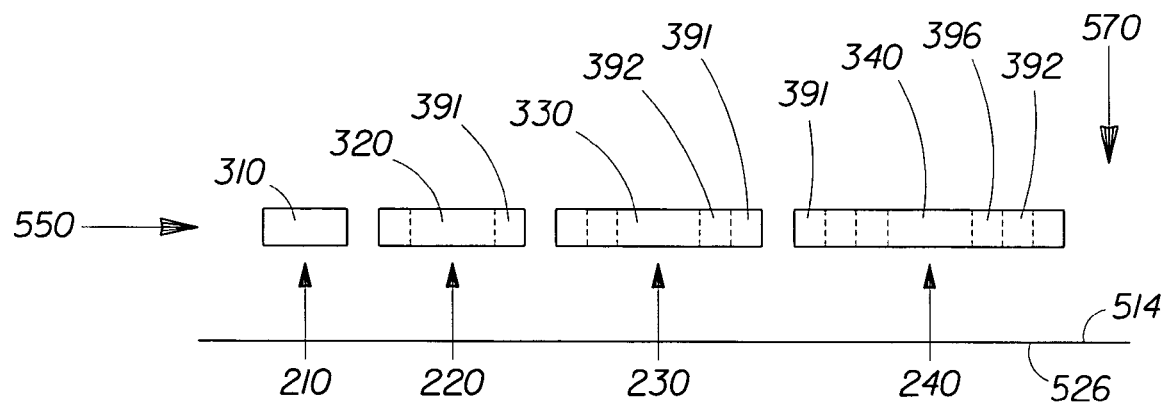
FIGS. 5A-5C show cross sectional views of the plurality of indicating members of FIG. 3C as seen through section line 5-5.
Figure 5B:
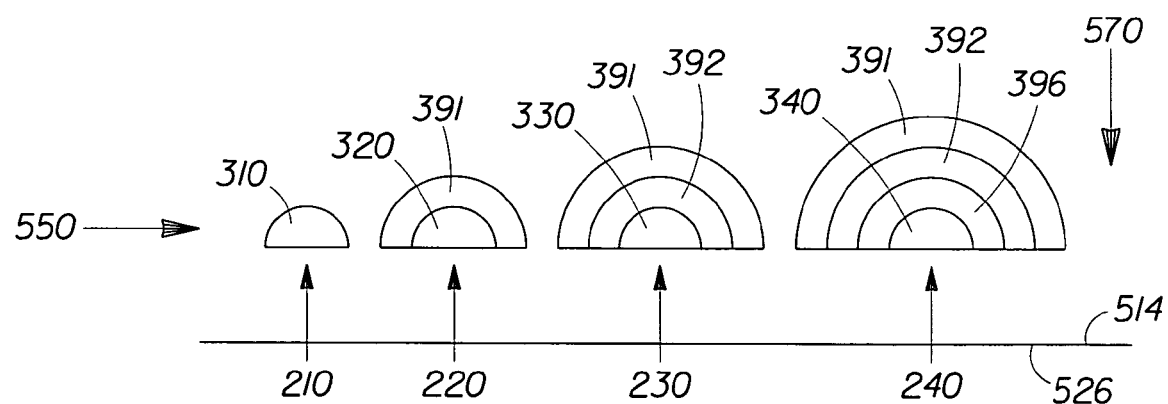

For example, as shown in FIGS. 5A-5B, the indicating members may comprise reactive elements that are completely or partially encapsulated by non-reactive portions or non-reactive elements. Note that if the indicating members comprise counter-acting elements, as discussed previously, then the first reactive element 310 may completely or partially encapsulate the counter-acting element corresponding thereto. Partial encapsulation of the reactive element, reactive layer, or counter-acting element, may or may not provide sufficient protection from premature activation by moisture.

As shown in FIG. 5A, the first, second, third, and fourth indicating members 210, 220, 230, and 240 can be positioned within an absorbent article adjacent an inner surface 514 of a backsheet 526. The second reactive member 320 can be partially encapsulated such that a wearer-facing surface and a backsheet-facing surface of the second reactive element 320 are exposed. Because the wearer-facing surface of second reactive element 320 is exposed, moisture from a first wetness event may prematurely activate the second reactive element 320 from the orthogonal direction 570. Consequently, an impermeable element may be incorporated into the indicating member such that moisture from an orthogonal direction 570 does not prematurely activate the second reactive member 320. Similarly, an impermeable member may be incorporated into the remaining indicating members where a need to preclude premature activation exists. If an impermeable element is incorporated into the indicating members, then moisture would be relegated to contacting the indicating members from a longitudinal direction 550 and the lateral direction (not shown).

In another embodiment, as shown in FIG. 5B, the first, second, third, and fourth indicating members are again positioned adjacent the inner surface 514 of the backsheet 526. The reactive elements 320, 330, and 340, are shown again exposed on their backsheet-facing surfaces; however, they are not exposed on their wearer-facing surfaces. For example, the first non-reactive portion 391 of the second indicating member 220 may cover the second reactive element 320 such that moisture from either the orthogonal direction 570 or the longitudinal direction 550 does not prematurely activate the second reactive element 320. Similarly, the non-reactive elements or portion, as described above, for the third and the fourth indicating members 230 and 240 may cover the third and fourth reactive elements 330 and 340, respectively. The coverage provided by the non-reactive elements or portions may preclude premature activation of the reactive elements. Therefore, moisture from a first wetness event can contact the second, third, or fourth indicating members 220, 230, and 240, from the orthogonal direction 570, the longitudinal direction 550, or the lateral direction (not shown), without prematurely activating the reactive elements of the second, third, and fourth indicating members 220, 230, and 240.

Figure 5C:
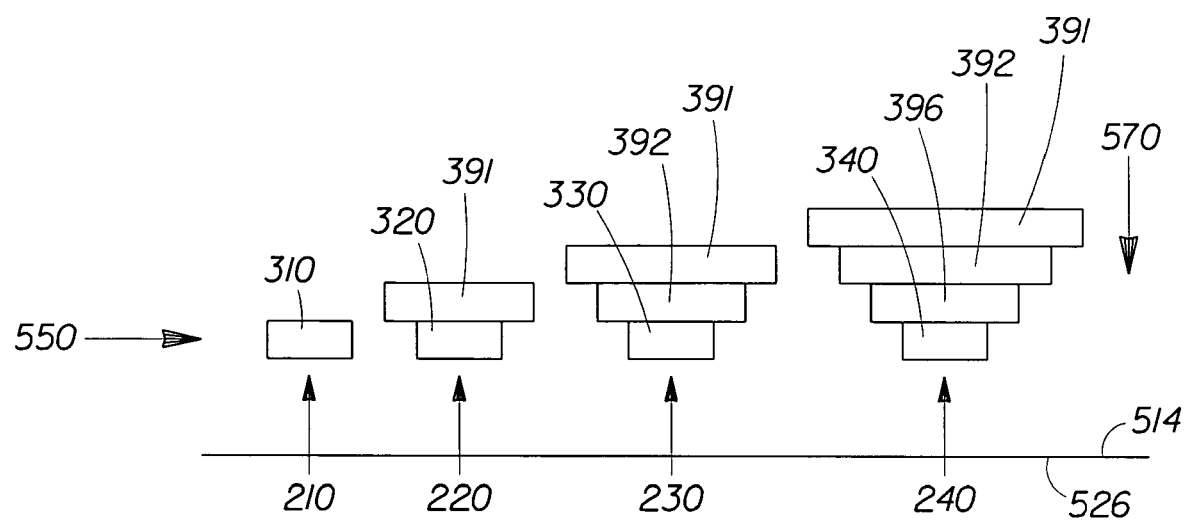

In yet another embodiment, as shown in FIG. 5C, the indicating members may comprise reactive elements, non-reactive elements, and counter-acting elements which are displaced from each other in the orthogonal direction 570. For example, the second indicating member 220 may be configured such that a backsheet-facing surface of the second reactive element 320 and a backsheet-facing surface of the first non-reactive portion 391 are not coplanar. Similar orthogonal displacement can be applied to the third and fourth indicating members 230 and 240. Additionally, the concept of orthogonal displacement may also be applied to the first indicating member 210 if the first indicating member comprises the first counter-acting element 411, as described in regard to FIG. 4A.

As shown in FIG. 5C, a wearer-facing surface of the first non-reactive portion 391 may preclude moisture from the orthogonal direction 570 from prematurely activating the second reactive element 320. However, the first non-reactive portion 391 may not preclude the activation of the second reactive element 320 from moisture approaching from the longitudinal direction 550 or the lateral direction (not shown). Consequently, an impermeable element may be incorporated into the indicating members such that premature activation by moisture from the longitudinal direction 550 and the lateral direction does not occur.

The configuration of the stack of reactive elements, non-reactive elements, and counter-acting elements is not limited to any particular orientation. For example, the reactive elements, 320, 330, 340, and 350, may be oriented such that they are adjacent the inner surface 514 of the backsheet 526, as shown. Alternatively, each indicating member 220, 230, and 240 can be arranged such that the non-reactive elements or portions are disposed adjacent to the inner surface 514 of the backsheet 526. In the alternative embodiment, an impermeable element may be incorporated into the indicating members to prevent moisture from activating the reactive areas from the orthogonal direction 570. Without an impermeable element, a first wetness event may cause moisture from the orthogonal direction 570 to contact more than the first reactive element 310, which may produce a false indication.

A suitable method for preventing moisture from prematurely activating the indicating members via moisture from the orthogonal direction 570 is to utilize an acquisition/distribution layer. The acquisition/distribution layer can be disposed between the topsheet and the absorbent core. The acquisition/distribution layer can be configured such that moisture from a wetness event is distributed to longitudinal edges of the absorbent core. In distributing moisture from a wetness event along the absorbent core, the acquisition/distribution layer minimizes the moisture available to the indicating members via the orthogonal direction 570. The acquisition/distribution layer is further discussed in U.S. Patent Application Publication No. 2005/0027267 A1 filed in the name of Van Dyke et al.

Note that in the embodiments discussed heretofore, the moisture provided by the wearer can dissolve the non-reactive members and non-reactive areas where present. For example, the wetness event counter can be exposed to an area in an absorbent article which retains moisture from a moisture source for five minutes. The non-reactive elements and non-reactive areas of this example can be selected such that they do not dissolve in less than ten minutes. In this manner, the wetness event counter may distinguish between a first wetness event and a second wetness event.

Suitable non-reactive elements, non-reactive portions, barrier layers, and protective layers, may include various materials such as surfactants and emulsifiers which will dissolve at different rates depending upon the relative proportion of hydrophilic to hydrophobic properties of the given molecule. For example, a solid polyethylene glycol of molecular weight of around 1000 will be very soluble in urine and dissolve quickly. Conversely, a solid hydrophobic paraffin or microcrystalline wax will have virtually no solubility in urine. In addition, various chemical classes of molecules can be designed to solubilize at desired rates. For instance, the fatty alcohol known as stearyl alcohol would dissolve very slowly in urine due to the molecule being dominated by the hydrophobic C18 alkyl chain. Although the hydroxyl group in stearyl alcohol contributes some hydrophilicity to the molecule, the molecular structure is dominated by the hydrophobic alkyl chain. To enhance its solubility in urine, the hydroxyl group of the stearyl alcohol could be ethoxylated to varying degrees to increase its solubility in urine. Generally, as more ethoxylate is reacted onto the C18 alkyl chain of the stearyl alcohol, the molecule becomes more soluble in urine. Thus, the solubility of the stearyl alcohol could be tailored to dissolve at different rates depending on the degree of ethoxylation. Uniqema (Wilmington, Del. U.S.A.) makes various ethoxylated fatty alcohols which would dissolve at different rates in urine depending on the alkyl chain length and degree of ethoxylation. Not to be limited by only ethoxylated alcohols, there are many other surfactants, emulsifiers and general classes of molecules which can be configured to dissolve at the desired and optimized rate after contacting urine.

Non dissolving non-reactive elements, non-reactive portions, barrier layers, and protective layers, may include, but are not limited to, non-polar materials as waxes, polyethylenes, high molecular weight fatty alcohols and fatty acids, and other hydrophobic materials. Solids of generally high solubility in urine would be those polar materials such as ethoxylated alcohols, polyethylene glycols, polyvinyl alcohol, water soluble inorganic salts, and other hydrophilic materials and other hydrophilic materials which include but are not limited to emulsifiers, solubilizers, surfactants, and polymers. Any suitable hydrophilic material operable in the embodiments discussed herein may be utilized in the present invention.

Alternatively, the non-reactive elements, non-reactive portions, barrier layers, and protective layers, contacted by moisture from wetness events could be selected such that they absorb moisture from the first wetness event and subsequently desorb the moisture thereby drying out. Upon drying out, the non-reactive members and areas could form fissures, e.g. cracks, crevices, openings, rifts, splits, etc., therein, such that moisture from future wetness events can pass through the fissures. Thus, on subsequent wetness events, moisture could reach a reactive element, non-reactive element, or non-reactive area through the fissures formed in the previous non-reactive element or non-reactive area.

A suitable material for use as the non-reactive elements, non-reactive portions, barrier layers, and protective layers, which form fissures after drying out, is clay. Clays are a class of materials known to shrink and swell depending upon the moisture content within its structure. In fact, at very dry conditions, clays can crack and fissure in order to create capillary pathways for urine flow. The montmorillonite clays are known to swell and contract dramatically depending upon the water content within their matrix. Another novel material that swells and contracts as a function of pH or calcium ion concentrations are forisomes. These are protein aggregates that are found in plants to protect leaves from nutrient loss. Cross linked polyacrylates are also suitable for use in the non-reactive elements, non-reactive portions, barrier layers, and protective layers.

The non-reactive elements, non-reactive portions, barrier layers, and protective layers, may need to be specifically sized such that their capacity to preclude premature activation of the reactive elements is not exceeded. For example, the non-reactive elements may be sized in accordance with data concerning the average urinary or fecal discharge of the wearer. Optionally, the indicating members may be strategically placed within the article such that moisture in excess of the non-reactive elements or areas capacity is absorbed by the absorbent core.

Figure 6:
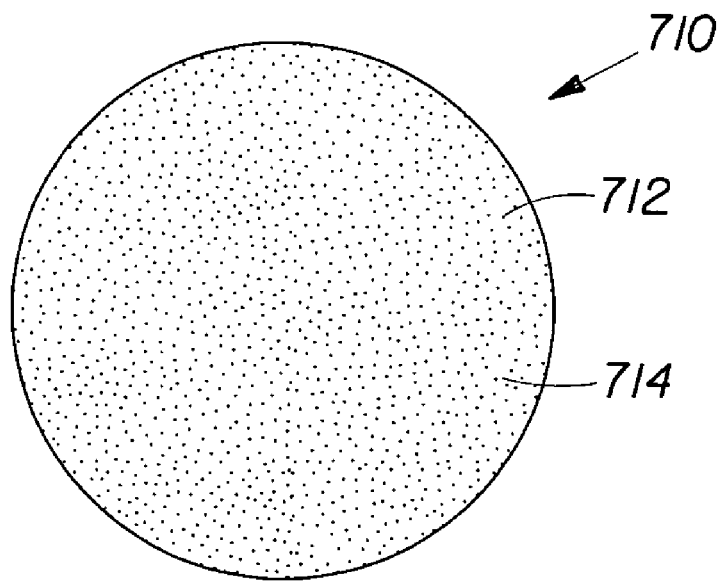
FIGS. 6-7 show embodiments of a reactive element which can be included in any of the indicating members of FIGS. 2A-2C.

As shown in FIG. 6, the reactive elements and reactive layers described heretofore may comprise a plurality of components such as a plurality of particles or printed pattern components. As an example, a reactive element 710, along with all of the reactive elements and reactive layers of the present invention, may include an indicating component 712 and a urine sensitive component 714 that function together to provide the caregiver a visual indication of the number of wetness events. The urine sensitive component 714 may be utilized such that moisture which is not from a wetness event, i.e. urination, does not trigger the indication. For example, the urine sensitive component 714 may be utilized such that perspiration from the wearer does not trigger a visible indication of a wetness event. Note that the urine sensitive component 714 can be used in conjunction with the materials discussed with regard to the non-reactive elements, non-reactive portions, barrier layers, and protective layers.

In one embodiment, the indicating component 712 may be in the form of particles suspended in the urine sensitive component 714. Moisture from a wetness event can activate the urine sensitive component 714, thereby causing the indicating component 712 to provide a visible indication of the wetness event. The indicating component 712 and the urine sensitive component 714 can be separate and different components from each other.

Figure 7:
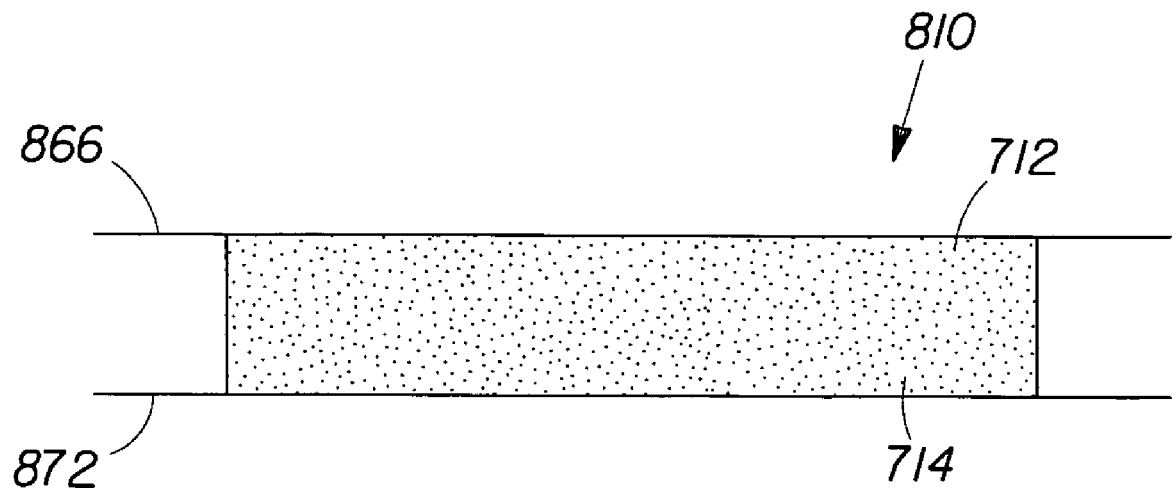

As shown in FIG. 7, a reactive element 810, or reactive layer, may be disposed on or in a substrate, or carrier elements 866 and 872. The carrier elements 866 and 872 may comprise a web-like component such as a film, woven, or nonwoven material, foam, scrim, or cellulosic material, to which a urinary sensitive component 714 or element is applied or affixed. Alternately, the carrier elements 866 or 872 may enclose or encapsulate the urine sensitive component 714 to prevent its migration or loss within the article before or during use. The carrier elements 866 and 872 may each comprise one layer folded back upon itself or may each comprise a multiplicity of layers. If more than one layer is employed, the various layers may have different properties or comprise different materials. For example, the urine sensitive component 714 may be disposed between a permeable top (i.e., wearer-facing) layer and an impermeable bottom layer. The indicating component 712 may be in the form of particles suspended in the urine sensitive component 714. The top layer may alternatively comprise a selectively permeable layer, a dissolving layer, a pH sensitive layer, or a coating. The carrier elements 866 and 872 may be flexible or may be relatively rigid.

The indicating component 712 of the reactive elements 710 and 810 may comprise a colorant, dye, or indicator that changes appearance (e.g., color) upon contact with urine. Examples of suitable indicating components include food grade dyes such as FD&C No. 1 Blue and pH indicators such as bromocresol green, bromophenol blue, and resazorine. Any suitable indicating component may be utilized including those materials discussed heretofore with regard to the indicating elements and/or indicating members.

In another embodiment, the indicating member may comprise the urine sensitive component 714 which is applied as a stripe or layer to a flexible substrate, such as a film. Plasticizers such as glycerol diacetate may be utilized to prevent the indicating member, or any component thereof, from cracking under mechanical stress and leading to false positives or negatives. In the context of a wetness event counter, a plasticizer may comprise any compound or composition that is at least partially soluble or miscible in the urine sensitive component and that reduces the tendency of the component to form crystallized regions, thereby reducing the glass transition temperature of the component and increasing its flexibility in the temperature range in which the article is expected to be used. Additional non-limiting examples of suitable plasticizers include polyhydroxy compounds such as glycerol and polyethylene glycols, microcrystalline waxes, ethylene vinyl acetates, isoparaffins, Guerbet alcohols, branched esters, branched alcohols, and other compounds such as those described above.

The indicating members, or any of the components, elements, or layers thereof, may be applied to a substrate, such as the article or any component thereof, or to a carrier element, via any means known in the art. Suitable processes for applying indicating members, components thereof, or elements thereof in a liquid or molten state to a substrate in either a continuous mode, intermittent mode, or in patterns, include slot coating, gravure printing, inkjet printing, spraying, screening, and the like. The indicating members, components thereof, elements thereof, or layers thereof, may be applied to a substrate or article in a solid form, such as films, webs, fibers, or particles, via continuous unwind processes, cut & slip processes, air deposition, and the like, and may be joined to the substrate via physical entanglement, entrapment, adhesives, or any other means as known in the art.

The urine sensitive component preferably changes properties in the presence of urine or is at least partially permeable by urine. For example, the urine sensitive component may dissolve or become more permeable in the presence of urine. The urine sensitive component may sense, or respond to, any of the components or properties of urine, including water, ion content, organic chemical content, ionic strength, pH, enzymes, urea, etc. Suitable materials for use in the urine sensitive component include starches and sugars, polyvinyl alcohol (in situ formed films and pre-manufactured films), gelatins, and other water or pH soluble films or materials. Other suitable materials include wetness or urine indicating compositions as known in the art, such as hot melt wetness indicators, water soluble dye systems, etc., including those described in U.S. Pat. Nos. 4,022,211; 4,743,238; 5,066,711; 5,342,861; 4,681,576; 5,035,691; 4,231,370; 4,895,567; and 6,075,178. Additionally, novel urine indicating compositions, such as those described U.S. Pat. No. 6,772,708 for a Wetness Indicator Having Improved Colorant Retention, may be employed as the urine sensitive component 714. For example, the urine sensitive component 714 may comprise stearyl alcohol, microcrystalline waxes, etholxylated alcohols, cationic quaternary amines, or mixtures thereof, and an indicating component, such as a pH indicator. In another example, the urine sensitive component may comprise a material or composite having different optical properties (e.g., contrast) in the wet state versus the dry state. For this example, the urine sensitive component may include films or tissues having patterns printed in permanent ink which appear, when viewed through the backsheet, darker when wetted thereby obviating the need for the indicating component.

Suitable material for use as the counter-acting elements are those materials listed as suitable for the non-reactive members, those materials listed as suitable for the indicating component, those materials listed as suitable for the urine sensitive component, or any combination thereof. Optionally, the counter-acting elements may comprise any material known in the art for modifying a visible signal of an indicating member.

Figure 8:
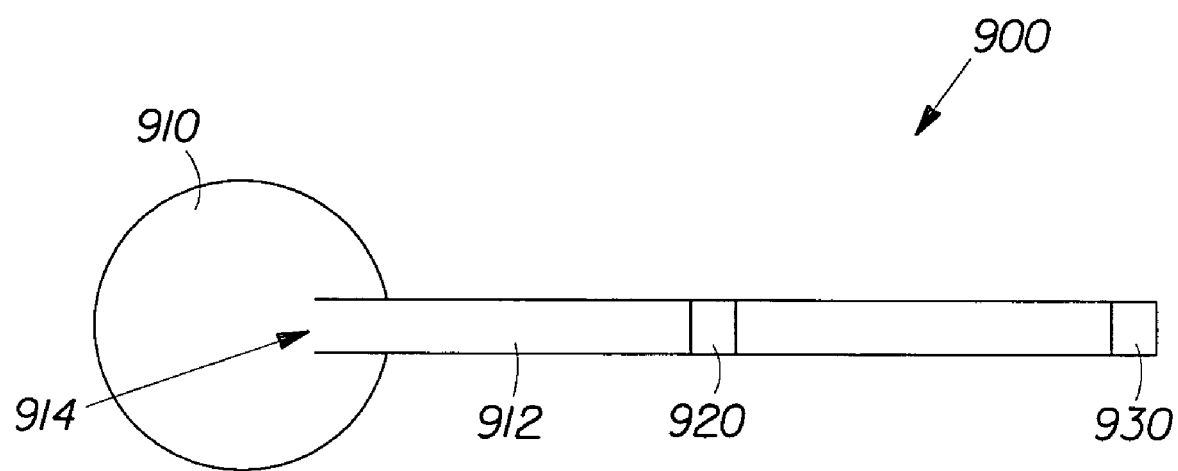
FIG. 8 shows an embodiment of the wetness event counter of FIG. 1 which includes a plurality of indicating members.

As shown in FIG. 8, a wicking member 912 may be utilized in a wetness event counter. An indicating apparatus 900 may comprise the wicking member 912, a first transferring member 920 and a second transferring member 930. Upon a first wetness event, a moisture source 910 is created thereby supplying moisture to an opening 914 in the wicking member 912. Moisture from the moisture source 910 can enter the opening 914 in the wicking member 912. The first transferring member 920 is in communication with the wicking member 912 such that the moisture can wick through the wicking member 912 to the first transferring member 920. When the moisture in the wicking member 912 reaches the first transferring member 920, the moisture activates the first transferring member 920.

The activation of the first transferring member 920 provides a visible indication of the first wetness event. In addition, the first transferring member 920 may absorb moisture from the moisture source 910. By absorbing moisture from the moisture source 910, the first transferring member 920 can preclude moisture from prematurely activating the second transferring member 930. The first transferring member 920 can be sized such that it is fully saturated upon absorbing all of the moisture from the moisture source 910. In addition, the first transferring member 920 may be sized such that the first transferring member 920 absorbs the moisture from within the wicking member 912.

On a subsequent wetness event, the moisture source 910 is re-supplied with moisture. Moisture is provided by the moisture source 910, thereby wicking through the wicking member 912. Additionally, the moisture can be transferred through the first transferring member 920 to the second transferring member 930. The second transferring member 930 is in communication with the wicking member 912 such that moisture transferred from the first transferring member 920 wicks toward the second transferring member 930. Moisture from the second wetness event activates the second transferring member 930, thereby causing the second transferring member 930 to provide a visible indication of the second wetness event.

Alternatively, the first transferring member 920 may be sized such that moisture remains in the wicking member 912 even after moisture from the moisture source 910 has been absorbed. Due to the meniscus effect, moisture within the wicking member 912 can remain even after the moisture source 910 is depleted. On a subsequent wetness event, the moisture source 910 is replenished such that the moisture within the wicking member 912 can advance to the second transferring member 930.

With regard to the embodiment shown in FIG. 8, the first and second transferring members may comprise a surfactant, an emulsifier, waxes, AGM, a sponge, a clay, a hydrogel, fluid stable aggregates, and high surface area polymeric foams, and mixtures thereof. Suitable high surface area foams for use in the present invention are further described in U.S. Pat. Nos. 5,387,207; 5,650,222; 6,013,589; and 6,083,211. The first transferring member 920 and the second transferring member 930 may comprise a reactive element or reactive layer, or any components of an indicating member, as described heretofore. The reactive element can allow the first transferring member 920 and the second transferring member 930 to provide a visible indication of a wetness event. For example, the transferring members 920, 930 may comprise a pH indicator which changes color after being contacted by the moisture.

Suitable AGM's are further described in U.S. patent application Ser. No. 10/950,011 entitled "Absorbent Articles Comprising Superabsorbent Polymer Having a Substantially Non-covalently Bonded Surface Coating" filed in the name of Beruda, et al. on Sep. 24, 2004, in U.S. patent application Ser. No. 10/941,672, entitled "Absorbent Articles Comprising Fluid Acquisition Zones with Superabsorbent" filed in the name of Beruda, et al. on Sep. 15, 2004 and in JP 2004-105118, entitled "An Aqueous-Liquid-Absorbing Agent and Its Production Process", filed in the name of Nippon Shokubai Co. Ltd. on Mar. 31, 2004.

The wicking member 912 may comprise a single channel or a plurality of channels. The wicking member 912 may comprise a capillary tube, a plurality of capillary tubes, or a wicking strip. The single tube or the plurality of tubes may be vapor impermeable. The first transferring member 920 and second transferring member 930 may be positioned in the wicking member 912. Alternatively, the wicking member 912 may comprise a first portion which extends from the moisture source 910 to the first transferring member 920 and a second portion which extends from the first transferring member 920 to the second transferring member 930.

In another embodiment, the first transferring member 920 may be selected such that it absorbs moisture from the moisture source 910 and expands in size such that excess moisture is unable to pass through the wicking member 912 to the second transferring member 930. Subsequently, the first transferring member 920 may desorb the absorbed moisture, thereby drying out. Upon drying out, the first transferring member 920 could form fissures therein allowing moisture to pass therethrough upon subsequent rewetting. Therefore, upon a second wetness event, moisture may pass through the fissures in the first transferring member 920 to the second transferring member 930, thereby actuating the same.

For this embodiment, the wicking member 912 may comprise a vapor permeable tube or plurality of tubes. The vapor permeability of the wicking member 912 could allow the first transferring member 920 to desorb the absorbed moisture from the first wetness event. Alternatively, the wicking member 912 may be coated with a hydrophobic coating to prevent moisture from other areas of the absorbent article from inadvertently wetting the wicking member 912 to cause further flow along the wicking member 912.

With regard to this embodiment, the wicking member 912 can be a vapor permeable material which is not soluble in water. Suitable examples are micro-porous films or a vapor permeable barrier layers as further described in U.S. application Ser. No. 10/844,182, entitled, "Breathable Absorbent Articles and Composites Comprising A Vapor Permeable, Liquid Barrier Layer", filed on May 12, 2004. The wicking member 912 may comprise any vapor permeable material known in the art which is operable in this embodiment.

With regard to this embodiment, suitable material for the first transferring member 920 and the second transferring member 930 are any material known in the art which absorbs moisture and increases in permeability when it dries out which would be operable in this embodiment. The first transferring member 920 and the second transferring member 930 may also comprise clay as discussed previously. Note that additional transferring members can be added to the embodiments discussed in regard to FIG. 8.

In another embodiment, the first transferring member 920 may contain a pH indicator or indicating component which changes color after being contacted by moisture. In this embodiment, the first transferring member 920 can preclude further urine migration along the wicking member 912 and can slowly dissolve after being contacted by urine from the first urination event. For example, the first transferring member 920 may be an ethoxylated alcohol surfactant of the optimum lipophilic/hydrophilic ratio such that it has the ability to stop the wicking of moisture during the first wetness event. However, after the first wetness event, the first transferring member 920 can completely dissolve, thereby preparing the wicking member 912 for moisture from the second wetness event.

In another embodiment, the first transferring member 920 may be selected such that it absorbs moisture from the moisture source 910 and effervesces in an optimum time frame to cause both a change in pH and break down of the 920 transferring member. Acids such as citric acid and the like can be used to react with sodium carbonate or sodium bicarbonate and mixtures thereof to cause the formation of carbon dioxide gas. The carbon dioxide gas is responsible for the fizzing action and can be used to break up the first transferring member 920 if properly formulated within the matrix of the material of the first transferring member 920. In this embodiment, an acid such as citric acid could also be impregnated onto the wicking member 912. Upon contact with moisture from a wetness event, which flows along the wicking member 912, the citric acid could dissolve and lower the pH of the moisture as it flowed toward the first transferring member 920. As a consequence of containing either sodium carbonate or sodium bicarbonate (or mixtures thereof or other appropriate effervescent agents) along with suitable solubilization agents (emulsifiers, surfactants, hydrophilic solvents), the effervescence reaction would commence as the low pH moisture contacted the first transferring member 920. The resulting pH change within the first transferring member 920 could be used to cause a visible indication via a pH indicator contained in the first transferring member 920. In addition, the gas production reaction could be used to break down the structure of the first transferring member 920 such that moisture from a second wetness event could wick to the second transferring member 930.

In another embodiment, the wicking member 912 may be coated with a color changing agent such as a pH indicator or indicating component as described herein. Alternatively, the wicking member 912 may be coated with an indicating composition such that after contact with moisture, a color change would occur. Thus, during the first urination event, a visible indication along the wicking member 912 could occur up to the point of this first transferring member 920 which can be configured to stop the flow of moisture during the time of the first urination event. Also, as discussed above, the first transferring member 920 can be configured to dissolve after the first wetness event. Similarly, during a second wetness event, the wicking member 912, between the first transferring member 920 and the second transferring member 930, can exhibit a visible indication of the second wetness event.

In another embodiment, numbers might be permanently printed on the backsheet or topsheet next to the first transferring member 920 and second transferring member 930 such that a numerical indication of a wetness event is visibly indicated. For example, a designation, #1, can be printed on the backsheet of the absorbent article adjacent the first transferring member 920 such that upon the first wetness event, the designation, #1, is highlighted to a caregiver. Similarly, upon a second wetness event, a designation, #2, which can be associated with the second transferring member 930, can be highlighted to a caregiver.

Additionally, the designations, #1 and #2 can be equally applied to any of the embodiments discussed herein. The designations may further include #3 and #4 which are associated with third and fourth indicating member as discussed herein. The designations may be printed on the article. For example, the designations may be printed on the topsheet, the backsheet, the core, or combinations thereof. Additionally, the designations may be printed on the indicating members themselves such that the designation is visibly indicated to a caregiver upon its corresponding wetness event.

A different signal or different visible indication as discussed herein can be a different color, shape, design, pattern, or combination thereof. Additionally, a different signal or a different visible indication may be longitudinally or laterally displaced from another signal and can be the same or a different color, shape, design, or pattern, as that signal. For example, a first signal may comprise a yellow dot. A second signal may similarly comprise a yellow dot; however, the second signal may be longitudinally or laterally displaced from the first signal.

Despite the fact that the embodiments and examples discussed heretofore disclose a signal of the wetness event counter which provides a visible indication of the wetness events, signals of the present invention can include many different types of indications as mentioned previously. Similar embodiments and examples to those discussed above are available with regard to a signal which comprises an indication which is visible, audible, tactile, olfactory, or a combination thereof. For example, high surface area foams as further described in U.S. Pat. Nos. 5,387,207; 5,650,222; 6,013,589; and 6,083,211, can be used to provide a tactile indication of a wetness event. Any devices, chemistries, etc., known in the art to produce visible, olfactory, audible, or tactile indications can be used in the present invention.

Figure 9:
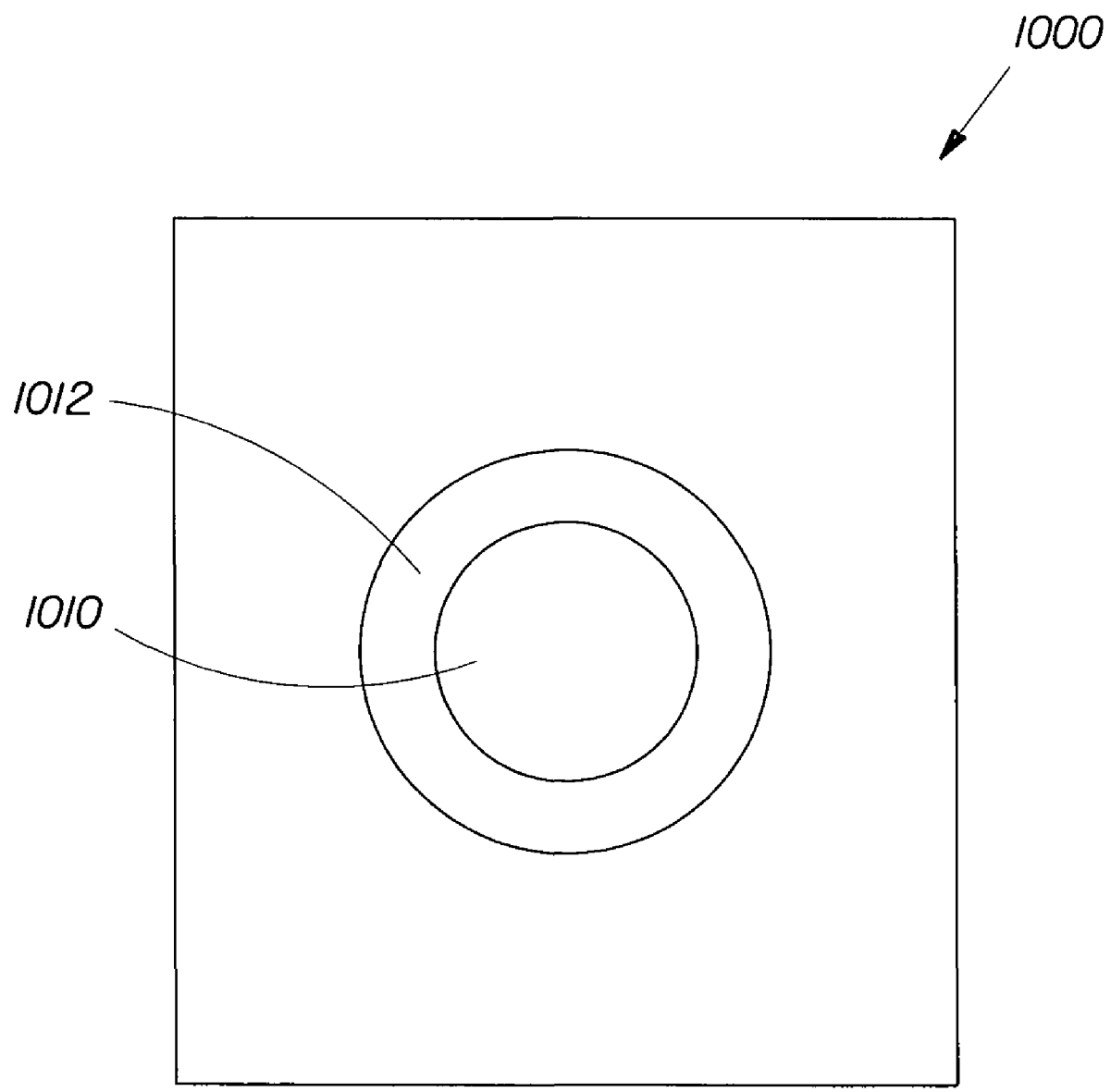
FIG. 9 is plan view showing another embodiment of a wetness event counter.

Embodiments are contemplated utilizing the expansion of the transferring members to produce a visible indication. For example, as shown in FIG. 9, a wetness event counter 1000, in some embodiments, may comprise a first indicating member 1010 which is visible through the backsheet of a disposable absorbent article when dry. The wetness event counter 1000 may further comprise a first expanding member 1012 disposed adjacent to the first indicating member 1010. As shown, in some embodiments, the first expanding member 1012 can surround the first indicating member 1010.

Upon a first wetness event, the first expanding member 1012 can expand such that the first indicating member 1010 is moved away from the backsheet of the disposable absorbent article. In moving away from the backsheet of the disposable absorbent article, the first indicating member 1010 becomes less visible through the backsheet of the disposable article. A disposable absorbent article may comprise a plurality of indicating members and expanding members. The indicating member and expanding members can be configured as described above and such that upon subsequent wetness events, the expanding members expand such that the indicating members are no longer visible through the backsheet of the disposable absorbent article.

Embodiments are contemplated where the first indicating member 1012 is not visible when the disposable absorbent article is in a dry state. Instead, upon a wetness event, the first expanding member 1012 can expand such that the first indicating member becomes visible through the backsheet.

Figure 10A:
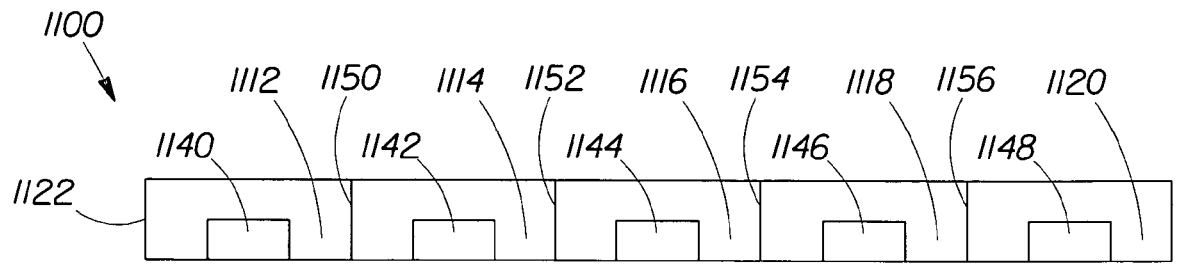
FIG. 10A is an elevation view showing another embodiment of a wetness event counter.
Figure 10B:
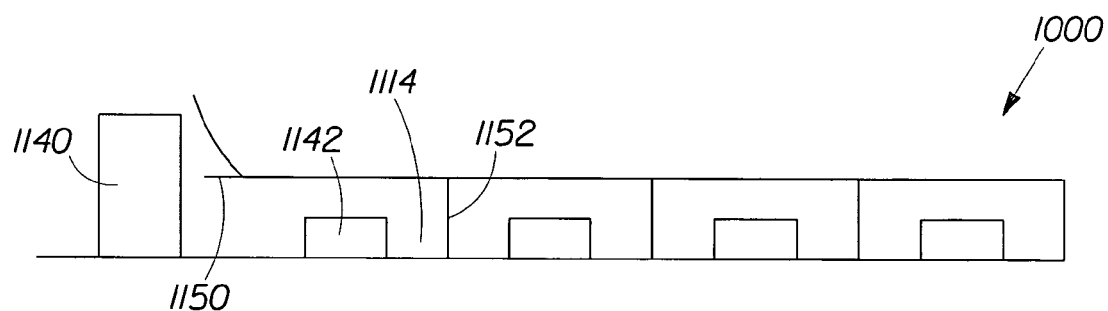
FIGS. 10B and 10C are elevation views showing the wetness event counter of FIG. 10A after a first wetness event and second wetness event, respectively.
Figure 10C:
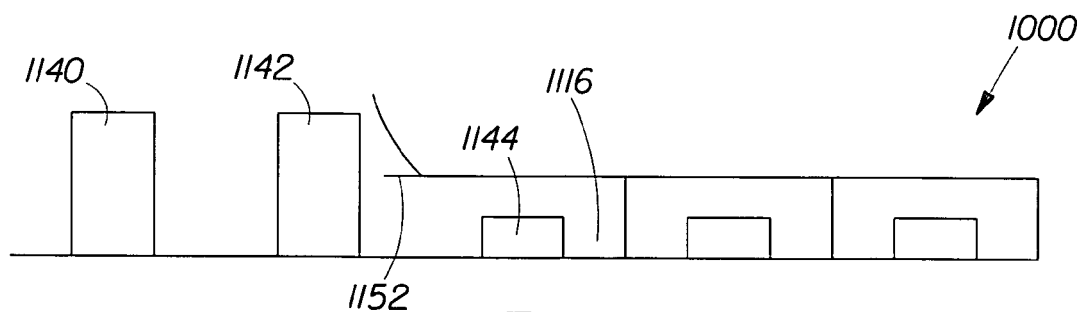

As shown in FIGS. 10A-10C, a wetness event counter 1100, in some embodiments, may comprise multiple indication cells 1112, 1114, 1116, 1118, and 1120. In some embodiments, expanding indicators are disposed within each indication cell. The expanding indicators are denoted 1140, 1142, 1144, 1146, and 1148. Between each indication cell, there can be a separation wall. For example, as shown, a separation wall 1150 can be between the first indication cell 1112 and the second indication cell 1114.

In some embodiments, the wearer or caregiver can remove a start tab 1122 of the wetness event counter 1100. The removal of the start tab 1122 can expose the first expanding indicator 1140 to any moisture that the wetness event counter 1100 will experience. In some embodiments, the caregiver or wearer may not need to remove a start tab. As shown in FIG. 10B, upon a first wetness event, the expanding indicator 1140 can expand thereby breaking the separation wall 1150 between the first indication cell 1112 and the second indication cell 1114. Breaking the separation wall 1150 between the first indication cell 1112 and the second indication cell 1114 can allow liquid from a second wetness event to contact and activate the second expanding indicator 1142.

As shown in FIG. 10C, similar to the first expanding indicator 1140, upon a second wetness event, the second expanding member 1144 can expand thereby breaking a separation wall 1152 between the second indicating cell 1114 and the third indicating cell 1116. Breaking the separation wall 1152 between the second indicating cell 1114 and the third indicating cell 1116 can allow liquid from a third wetness event to contact and activate the third expanding indicator 1144.

Any suitable material listed above for the expanding members or expanding indicators can be utilized in these embodiments. For example, the expanding members and/or expanding indicators may comprise AGM.

A variety of materials can be utilized in the manufacture of the absorbent articles described herein. Some examples of the materials which can be used in the manufacture of absorbent articles are provided below; however, the list of materials provided is by no means exhaustive. For example, breathable materials, which are used extensively in absorbent articles may include materials such as woven webs, nonwoven webs, composite materials such as film-coated nonwoven webs, microporous films such as manufactured by Mitsui Toatsu Co., of Japan under the designation ESPOIR NO™ and by Exxon Chemical Co., of Bay City, Tex., U.S.A. under the designation EXXAIRE™, and monolithic films such as manufactured by Clopay Corporation, Mason, Ohio, U.S.A. under the name HYTREL™ blend P18-3097. Some breathable composite materials are described in greater detail in U.S. Pat. No. 6,187,696; U.S. Pat. No. 5,938,648; U.S. Pat. No. 5,865,823; and U.S. Pat. No. 5,571,096.

The backsheet is generally that portion of the diaper positioned adjacent a garment-facing surface of the absorbent core that prevents the exudates absorbed and contained therein from soiling articles that may contact the diaper, such as bedsheets and undergarments. The topsheet is preferably positioned adjacent body-facing surface of the absorbent core and may be joined thereto and/or to the backsheet by any attachment means known in the art. The topsheet, the backsheet, and the absorbent core may be assembled in a variety of configurations, as further described generally in U.S. Pat. No. 3,860,003, U.S. Pat. No. 5,151,092, U.S. Pat. No. 5,221,274, U.S. Pat. No. 5,554,145, U.S. Pat. No. 5,569,234, U.S. Pat. No. 5,580,411, and U.S. Pat. No. 6,004,306.

The absorbent core may comprise any absorbent material which is generally compressible, conformable, non-irritating to the wearer's skin, and capable of absorbing and retaining liquids such as urine and other certain body exudates. The absorbent core may be manufactured in a wide variety of sizes and shapes and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core are described in U.S. Pat. No. 4,610,678, U.S. Pat. No. 4,673,402, U.S. Pat. No. 4,834,735, U.S. Pat. No. 4,888,231, U.S. Pat. No. 5,137,537, U.S. Pat. No. 5,147,345, U.S. Pat. No. 5,342,338, U.S. Pat. No. 5,260,345, U.S. Pat. No. 5,387,207, and U.S. Pat. No. 5,625,222.

As noted above, the diaper may also include a fastening system. The fastening system preferably maintains the first waist region and the second waist region in a configuration so as to provide lateral tensions about the circumference of the diaper to hold the diaper on the wearer. The fastening system preferably comprises a surface fastener such as tape tabs, hook and loop fastening components and/or hermaphroditic fastening components, although any other known fastening means are generally acceptable. In alternative embodiments, opposing sides of the article may be seamed or welded to form a pant. This allows the article to be used as a pull-on type diaper, such as a training pant.

Some exemplary surface fastening systems are disclosed in U.S. Pat. No. 3,848,594, U.S. Pat. No. 4,662,875, U.S. Pat. No. 4,846,815, U.S. Pat. No. 4,894,060, U.S. Pat. No. 4,946,527, U.S. Pat. No. 5,151,092, and U.S. Pat. No. 5,221,274. An exemplary interlocking fastening system is disclosed in co-pending U.S. Pat. No. 6,432,098. The fastening system may also: provide a means for holding the article in a disposal configuration as disclosed in U.S. Pat. No. 4,963,140; include primary and secondary fastening systems, as disclosed in U.S. Pat. No. 4,699,622; provide means to reduce shifting of overlapped portions or to improve fit as disclosed in U.S. Pat. No. 5,242,436; and provide means to resist gapping at a wearer's belly as disclosed in U.S. Pat. No. 5,499,978, U.S. Pat. No. 5,507,736, and in U.S. Pat. No. 5,591,152.

Examples of diapers with elasticized side panels are disclosed in U.S. Pat. No. 4,857,067, U.S. Pat. No. 4,381,781, U.S. Pat. No. 4,938,753, U.S. Pat. No. 5,151,092, U.S. Pat. No. 5,221,274, U.S. Pat. No. 5,669,897, and U.S. Pat. No. 6,004,306.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. No. 5,514,121, U.S. Pat. No. 5,171,236, U.S. Pat. No. 5,397,318, U.S. Pat. No. 5,540,671, U.S. Pat. No. 6,168,584, U.S. Pat. No. 5,306,266, and U.S. Pat. No. 5,997,520. Examples of compartments or voids are disclosed in U.S. Pat. No. 4,968,312, U.S. Pat. No. 4,990,147, U.S. Pat. No. 5,062,840, and U.S. Pat. No. 5,269,755. Examples of suitable transverse barriers are described in U.S. Pat. No. 5,554,142, U.S. Pat. No. 6,010,490, and U.S. Pat. No. 5,653,703. Examples of other structures especially suitable for management of low viscosity feces are disclosed in U.S. Pat. Nos. 5,941,864, 5,977,430, and 6,013,063.

EXAMPLES

Example 1

An indicating member suitable for use in a disposable absorbent article may be constructed as follows:

1. 0.02 grams of a food grade dye that displays a noticeable color when dissolved in water is dispersed in 100 grams of molten 1-tetradecanol. Preferably, the dye has a blue, green, or purple color when dissolved in water. An example of a suitable blue dye is FD&C No. 1 Blue, which is principally the disodium salt of ethyl[4-[p-[ethyl (m-sulfobenzyl)amino]-α-(o-sulphophenyl)benzylidene]-2,5-cyclohexdien-1-ylidene](m-sulphobenzyl) ammonium hydroxide inner salt. This compound is commonly designated CAS#2650-18-2.
2. The molten tetradecanol is cooled and formed into small particles, preferably smaller than 1 mm in largest dimension. Alternatively, the mixture may be spray-dried to form roughly spherical particles. Preferred particle sizes are approximately 200 microns.

3. The particles from step 2 are coated, e.g., in a fluidized bed, with additional molten 1-tetradecanol and cooled. The thickness of the coating may vary from several microns to about 1 mm.
4. The particles from step 3 are coated with a polyvinyl alcohol film coating.
5. The particles are encapsulated between a layer of nonwoven and a layer of polypropylene film, each having the dimensions of 1 cm by 4 cm. The layers are thermomechanically, adhesively, ultrasonically, or otherwise bonded together.
6. The composite from step 5 is affixed to the underside of a diaper topsheet in the crotch region via hot melt adhesive.

Example 2

An indicating member suitable for use in a disposable absorbent article may be constructed as follows:
1. 0.2 grams of bromophenol blue pH indicator is dispersed in 100 grams of molten 1-tetradecanol.
2. The mixture from step 1 is applied in a molten form in an 0.5 by 3 cm stripe at a basis weight of 25 grams per square meter to a piece of polypropylene film. The mixture is allowed to cool and harden.
3. A layer of polyvinyl alcohol film is applied over the strip from step 2.
4. The composite from step 3 is affixed to the underside of a diaper topsheet in the crotch region of the diaper via a hot melt adhesive.

Example 3

An indicating member suitable for use in a disposable absorbent article may be constructed as follows:
1. 0.2 grams of bromophenol blue pH indicator is dispersed in 100 grams of molten 1-tetradecanol to form mixture A.
2. 0.2 grams of bromophenol blue pH indicator is dispersed in 100 grams of molten glycerol diacetate to form mixture B.
3. Mixture A is applied in a molten form in an 0.5 cm diameter dot at a basis weight of 25 grams per square meter to a piece of polypropylene film having the dimensions of about 2 cm by about 5 cm. The mixture is allowed to cool and harden.
4. Mixture B is applied in a molten form in a 0.5 cm diameter dot at a basis weight of 25 grams per square meter to the same piece polypropylene film. A 1 cm gap is left between the dots formed with mixtures A and B. The mixture is allowed to cool and harden.
5. Dots of molten 1-tetradecanol and glycerol diacetate having diameters of 1.0 cm and a basis weight of 25 gsm are applied directly over the dots A and B, respectively, from steps 3 and 4 and allowed to cool and harden.
6. A layer of polyvinyl alcohol film is applied over the dots from step 5.
7. The composite from step 6 is affixed to the underside of a diaper topsheet in the crotch region of the diaper via a hot melt adhesive.

Example 4

An indicating member suitable for use in a disposable absorbent article may be constructed as follows:
The inner surface of a 1.0 mil thick polypropylene film is coated with a film of a molten wetness indicating adhesive having a basis weight 26 grams per square meter and width of 5 millimeters. Any known wetness indicating adhesive adapted to provide a color change when contacted by urine, including those described herein, is suitable, especially those adhesives comprising a pH indicator, such as bromocresol green and bromophenol blue, having a color transition in the range of about pH 3 to about pH 6. Examples of suitable commercially available wetness indicating adhesives include FINDLEY™ 9219-01, 9052, and 9133-05 adhesives available from Bostik-Findley of Middleton, Mass., U.S.A.

After the film from step 1 has solidified, it is completely covered by a layer of 1-tetradecanol. This 1-tetradecanol layer has a basis weight of between 26 to 39 grams per square meter, and a width of 15 millimeters. The 1-tetradecanol layer is oriented such that its width extends 5 mm on either side of the width of the wetness indicating adhesive layer.

The resultant composite, or a portion thereof, may be affixed to the inner surface of a disposable diaper topsheet or backsheet.

Example 5

An indicating member suitable for use in a disposable absorbent article may be constructed as follows:
1. An indicating composition can be prepared according to the formula and procedure described below:

| Ingredient | Grams |
| --- | --- |
| Stearyl Alcohol | 49.8 |
| Microcrystalline Wax | 10.0 |
| Stearyl Phosphate | 10.0 |
| Dimethyl(2-ethylhexylhydrogenated tallowalkyl)ammonium methyl sulfate | 10.0 |
| Bromocresol Green (powdered acid form) | 0.2 |
| C20-C40 Pareth-40 nonionic surfactant | 20.0 |

This urine indicating composition is made by first weighing out the correct amounts of stearyl alcohol, microcrystalline wax, and stearyl phosphate into a stainless steel container. The stearyl alcohol should be a white waxy solid with a purity of at least 97% and no more than 2% of arachidyl alcohol, and have a melting point in the range of about 56° C. to about 60° C. The product designated CO1897 stearyl alcohol available from The Procter & Gamble Company of Cincinnati, Ohio, U.S.A., is a current example of a suitable material. The microcrystalline wax should be a high molecular weight petroleum based wax consisting of saturated branched and cyclic non-polar hydrocarbons and possessing a melting point in the range of about 60° C. to about 95° C. The product designated MULTIWAX™ W-835 available from the Crompton Corporation of Petrolia, Pa., U.S.A. is an example of a suitable microcrystalline wax. This mixture is heated and mixed at a temperature in the range of about 100° C. to about 110° C. until the mixture is a clear, transparent and colorless molten mixture. The dimethyl(2-ethylhexylhydrogenated tallowalkyl)ammonium methyl sulfate is then added to the above molten mixture and heated at a temperature in the range of about 100° C. to about 110° C. for 10 minutes. The dimethyl(2-ethylhexylhydrogenated tallowalkyl)ammonium methyl sulfate should have a quaternary salt content of 81.5-84.5%, possess a free amine and free amine salt impurity content of no more than 4%, and have an HLB of 17-18. The product designated ARQUAD™ HTL8(W)-MS available from Akzo-Nobel of Chicago, Ill., U.S.A. is a good example of a dialkyldimethyl quaternary ammonium salt currently meeting these requirements. To this mixture, the bromocresol green pH indicator is added. The resultant mixture is heated while mixing at a temperature in the range of about 100° C. to about 110° C. for 20 mixtures. Finally, to this mixture, C20-C40 Pareth-40 surfactant is added, the surfactant having been preheated to a temperature in the range of about 100° C. to about 110° C. The C20-C40 Pareth-40 surfactant should have molecular weight ($M_n$) between about 2200 and about 2400, an ethylene oxide content between in the range of about 75% to about 85%, an HLB of approximately 16, and a melting point in the range of about 80° C. to about 94° C. The product designated PERFORMATHOX™ 480 available from New Phase Technologies of Sugar Land, Tex., U.S.A is an example of a suitable C20-C40 Pareth-40 meeting these requirements. The entire composition is subsequently heated at a temperature in the range of about 100° C. to about 110° C. until it is clear, transparent and yellow-orange in color.

2. A 5 mm wide stripe of the composition from step 1 above is applied to the inner surface of a 1.0 mil thick polypropylene film is coated with at a basis weight of 26 grams per square meter and width of 5 millimeters.

3. After the film from step 2 has solidified, it is completely covered by a continuous layer of 1-tetradecanol. This 1-tetradecanol layer has a basis weight of between 26 to 39 grams per square meter, and a width of 15 millimeters. The 1-tetradecanol layer is oriented such that its width extends 5 mm on either side of the width of the indicating composition layer.

Example 6

An indicating composition suitable for use in an indicating member in a disposable absorbent article may be constructed as follows:
1. An indicating composition can be prepared according to the formula and procedure described above in example 5. The composition can be coated onto the transferring members as discussed in regard to FIG. 8. The indicating composition could be used as the barrier to capillary urine flow during the course of a particular wetness event. The indicating composition could further change color to indicate a particular wetness event and slowly dissolve in preparation for the next wetness event. The solubility of this indicating composition could be optimized by changing the concentration of emulsifiers in the formula (C20-C40 Pareth-40 nonionic surfactant).
2. The indicating composition could be coated onto the transferring members, as discussed above, to act as a barrier of further flow. In addition, the indicating composition can also function as the reactive element and as readying the device for the next wetness event by slowly dissolving.

Example 7

An indicating member suitable for use in a disposable absorbent article may be constructed as follows:
1. An indicating composition can be prepared according to the formula and procedure described above in example 5. The indicating composition could be used as a coating for either the wicking member or the inside walls of a capillary tube for a region of the wicking member between the moisture source and first transferring member, for a region of the wicking member between the transferring members, and a region of the wicking member between any additional transferring members that may be present. A coating level between 10 and 40 grams per square meter would likely be acceptable. Thus, as urine contacted this indicating composition, a color change could occur along the wicking member up to the point of the transferring member. In addition, a protective wax or hydrophobic transparent coating may be required to prevent extraneous moisture from prematurely activating a reactive element of a transferring member. A thin coating of microcrystalline wax or other transparent waxes or hydrophobic polymers or materials can be used to protect any reactive elements from extraneous moisture. A suitable wax is sold under the designation of W835 and manufactured by Crompton, Inc., Petrolia, Pa., U.S.A. The need for such a coating may be obviated if the wicking member is a capillary tube having the indicating component coated on its inner wall.

2. The transferring members may comprise a urine sensitive component which includes, a solid and urine soluble material such as the BRIJ™ emulsifiers, from Uniqema, Wilmington, Del., U.S.A. ethoxylated alcohols or solid and urine soluble material such as the CARBOWAX™ materials from DOW, Midland, Mich., U.S.A. In addition, polyethylene glycols could be used to prevent excess urine flow during the course of a wetness event but slowly dissolve to ready the wetness event counter for the next event. In addition, other emulsifiers, solubilizers, and combinations of emulsifiers and solubilizers, could be used to function as the urine sensitive component.

3. Optionally, a pH indicator such as bromocresol green, or bromophenol blue, or any other suitable pH indicator and mixtures thereof, could be formulated into the transferring members at a level of approximately 0.2%. During storage, an acidic emulsifier such as cetyl phosphate, MAP 160™ from Uniqema, Wilmington, Del., U.S.A. or stearyl phosphate, MAP 180™ from Uniqema, Wilmington, Del. U.S.A. may be required to stabilize the pH indicator in its acid yellow form until the basic urine neutralized it to its anionic and blue form. Other acidic type emulsifiers or organic acids would also be suitable stabilizing agents.

4. Alternatively, an effervescence composition can be added to the BRIJ™ or CARBOWAX™ compositions described in step 3. A composition of 30% sodium Bicarbonate, 25% citric acid, and 45% of either a BRIJ™ or CARBOWAX™ or mixtures thereof, can be utilized in the transferring members. Other organic acids can be used in place of the citric acid, the other acids include tartaric acid, fumaric acid, malic acid, maleic acid, adipic acid, etc. Also, the sodium bicarbonate can be used in combination with sodium carbonate.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. An absorbent article adapted for wearing about the lower torso of a wearer, the absorbent article having a chassis, the chassis comprising:
   a topsheet;
   a backsheet attached to at least a portion of the topsheet;
   an absorbent core disposed between the topsheet and the backsheet; and
   a wetness event counter attached to the chassis and which is adapted to provide a different signal for each of a plurality of successive wetness events experienced by the absorbent article, wherein the wetness event counter comprises a plurality of wetness indicating members, each of the members comprising a reactive element and a non-reactive element that precludes premature activation by urine of the reactive element of each successive wetness indicating member.

2. The absorbent article of claim 1, wherein a first indicating member provides a first signal when activated by a first wetness event, and wherein a second indicating member provides a second signal when activated by a second wetness event.

3. The absorbent article of claim 2, wherein the first signal is visible through the backsheet of the absorbent article.

4. The absorbent article of claim 2, wherein the plurality of indicating members are visible through the backsheet of the disposable absorbent article when not activated and are not visible through the backsheet when activated.

5. The absorbent article of claim 2, wherein the plurality of indicating members are not visible through the backsheet when not activated and become visible through the backsheet when activated.

6. The absorbent article of claim 1, wherein the wetness event counter is disposed between the absorbent core and the backsheet of the absorbent article.

7. The absorbent article of claim 6 further comprising an expanding member disposed adjacent to the indicating member, wherein the expanding member is capable of moving the indicating member away from the backsheet such that the indicating member is no longer visible through the backsheet.

8. The absorbent article of claim 6 further comprising an expanding member disposed adjacent to the indicating member, wherein the expanding member is capable of moving the indicating member closer to the backsheet such that the indicating member is visible through the backsheet.

9. The disposable absorbent article of claim 1, wherein the wetness event counter is disposed on at least a portion of the topsheet.

10. A disposable pull-on diaper having a wearer-facing surface and a garment-facing surface; a longitudinal axis and a lateral axis; a front waist region; a back waist region, and a crotch region disposed between the front and back waist regions, wherein the front waist region and back waist region are joined to form a waist opening and leg openings, the disposable pull-on diaper further comprising:
    a topsheet;
    a backsheet having an inner surface and an outer surface, wherein the backsheet is attached to at least a portion of the topsheet;
    an absorbent core disposed between at least a portion of the topsheet and the backsheet; and
    a wetness event counter attached to the inner surface of the backsheet, wherein the wetness event counter is adapted to provide a signal for each wetness event experienced by the diaper and wherein the wetness event counter comprises:
        a first indicating member comprising a first reactive element that provides a visible signal when dry and an obstructed first signal when activated by a first wetness event, and a first non-reactive element;
        a second indicating member comprising a second reactive element that provides a visible signal when dry and an obstructed second signal when activated by a second wetness event, and a second non-reactive element,
    wherein the first non-reactive element prevents activation of the second indicating member by urine of a first wetness event.

11. The disposable pull-on diaper of claim 10 further comprising:
    a third indicating member comprising a third reactive element that provides a visible signal when dry and an obstructed third signal when activated by a third wetness event, and a third non-reactive element; and
    a fourth indicating member comprising a fourth reactive element that provides a visible signal when dry and an obstructed fourth signal when activated by a fourth wetness event,
    wherein the second non-reactive element prevents activation of the third and fourth indicating member by urine of a second wetness event and wherein the third non-reactive element prevents activation of the fourth indicating member by urine of a third wetness event.

12. The disposable pull-on diaper of claim 10 further comprising a first expanding member disposed adjacent to the first indicating member, wherein upon the first wetness event, the expanding member expands such that the first indicating member is moved away from the backsheet such that the first indicating member is no longer visible through the backsheet.

* * * * *